(12) United States Patent
Choubey et al.

(10) Patent No.: US 8,069,057 B2
(45) Date of Patent: Nov. 29, 2011

(54) SYSTEMS AND METHODS FOR PROVIDING HEALTHCARE ASSET INTELLIGENCE USING SERVICE-ORIENTED ARCHITECTURE AND SERVICE-ORIENTED COMPUTING

(75) Inventors: Suresh K. Choubey, Delafield, WI (US); Narendra B. Joshi, Sussex, WI (US)

(73) Assignee: General Electric Company, Schenectady, NY (US)

( * ) Notice: Subject to any disclaimer, the term of this patent is extended or adjusted under 35 U.S.C. 154(b) by 718 days.

(21) Appl. No.: 12/099,025

(22) Filed: Apr. 7, 2008

(65) Prior Publication Data

US 2009/0254362 A1  Oct. 8, 2009

(51) Int. Cl.
*G06Q 50/00* (2006.01)
(52) U.S. Cl. .............................................. 705/2; 705/3
(58) Field of Classification Search .................. 705/2–4, 705/28; 235/385
See application file for complete search history.

(56) References Cited

U.S. PATENT DOCUMENTS

2005/0228808 A1* 10/2005 Mamou et al. ................ 707/100
2007/0027714 A1*  2/2007 Fenno .............................. 705/2
2009/0327102 A1* 12/2009 Maniar et al. ................... 705/28

OTHER PUBLICATIONS

Michael N. Huhns and Munindar P. Singh, "Service-Oriented Computing: Key Concepts and Principles," IEEE Internet Computing, vol. 9, No. 1, 2005, pp. 75-81, available at http://dsonline.computer.org/portal/site/dsonline/menuitem. 6dd2a408dbe4a94be487e0606bcd45f3/index.jsp?&pName=dso_level1_article&TheCat=1015&path=dsonline/2005/0501&file=w1soc.xml& (last accessed Apr. 10, 2008 ).

* cited by examiner

*Primary Examiner* — Gerald J. O'Connor
*Assistant Examiner* — Michelle Le
(74) *Attorney, Agent, or Firm* — McAndrews, Held & Malloy, Ltd.; William Kryger

(57) ABSTRACT

Certain embodiments of the present invention provide a system for providing healthcare asset intelligence comprising a data layer adapted to preprocess healthcare asset intelligence data, a service component layer adapted to comprise a plurality of service components, and a service application layer adapted to comprise a service application. The healthcare asset intelligence data is data related to management of healthcare assets. The system is configured according to a service-oriented architecture and uses service-oriented computing. Each of the plurality of service components is adapted to utilize the preprocessed healthcare asset intelligence data. The service application is adapted to utilize at least one of the plurality of service components to provide the healthcare asset intelligence.

21 Claims, 14 Drawing Sheets

SYSTEMS AND METHODS FOR PROVIDING HEALTHCARE ASSET INTELLIGENCE USING SERVICE-ORIENTED ARCHITECTURE AND SERVICE-ORIENTED COMPUTING

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to managing healthcare assets. More specifically, the present invention relates to systems, methods, and apparatuses for providing healthcare asset intelligence.

Healthcare environments such as hospitals must manage many different healthcare assets, often in very large quantities. In a healthcare setting, healthcare assets may include personnel, equipment, devices, and supplies. Because such a diversity of healthcare assets is present in all healthcare environments, managing these assets effectively can be quite burdensome. As a result, healthcare assets are not utilized in an efficient way in most healthcare environments for a variety of reasons. For example, each hospital in an enterprise may manage existing data sources in a customized manner that may not be compatible with other hospitals in the enterprise. As another example, there may be a scarcity of intravenous (IV) pumps in one hospital within an enterprise of hospitals and a surplus of the same IV pumps in another hospital within the enterprise. The most efficient solution to these problems may be for the hospital having extra IV pumps to meet the demand of the hospital having a scarcity of IV pumps. However, unless the two hospitals are aware of one another's supplies and demands, the most efficient distribution of IV pumps across the enterprise may not be achieved. That is, global sharing at the enterprise level may not be possible.

In general, the various data sources used by a healthcare environment to manage its assets are heavily customized to that particular environment, preventing the rapid development of applications that can be used across varying types of data sources. In many cases, even different departments within a single hospital may utilize data sources that are vastly different from one another. In such a situation, the execution of an application utilizing data from each of these different departments may be impossible or impractical because the data sources are so heavily customized. This problem may be even more apparent for enterprises that include multiple independent healthcare environments. However, converting all of these disparate data sources into a single format that will support such application development and execution is both impractical and overly expensive for most healthcare environments and enterprises.

Healthcare asset intelligence data is generated and can be expressed in a wide variety of ways. For example, healthcare asset intelligence data may include the number of hospital beds in a hospital, the hospital's annual operating budget, the work schedules of hospital personnel, the locations of the hospital's X-ray scanners, and the number of units of Type A blood available for transfusion, among other information. Healthcare asset intelligence data within an enterprise may be even more voluminous and varied. As a result, converting every source providing healthcare asset intelligence data to a hospital or enterprise into a single format may be exceptionally burdensome.

Because total data conversion is impractical and not cost-efficient, healthcare environments are unable to utilize valuable healthcare asset intelligence data in order to maximize their assets, achieve their business goals, and provide the highest quality care to their patients. With each healthcare environment maintaining its own healthcare asset intelligence data in a proprietary format, distinct departments within hospital (or distinct hospitals within an enterprise) are unlikely to connect their needs and interests, learn from one another's operations, pool resources for mutual benefit, or maximize asset lifespan and efficiency, simply because of their healthcare asset intelligence deficiencies.

BRIEF SUMMARY OF THE INVENTION

Certain embodiments of the present invention provide a system for providing healthcare asset intelligence comprising a data layer, a service component layer, and a service application layer. The data layer is adapted to preprocess healthcare asset intelligence data. The service component layer is adapted to comprise a plurality of service components. The service application layer is adapted to comprise a service application. The healthcare asset intelligence data is data related to management of healthcare assets. The system is configured according to a service-oriented architecture and uses service-oriented computing. Each of the plurality of service components is adapted to utilize the preprocessed healthcare asset intelligence data. The service application is adapted to utilize at least one of the plurality of service components to provide the healthcare asset intelligence.

Certain embodiments of the present invention provide healthcare asset intelligence including selecting a service component from a plurality of service components and configuring a service application based at least in part on the selected service component using service-oriented computing. The plurality of service components is in a service-oriented architecture. The service component is adapted to acquire healthcare asset intelligence data from a data warehouse. The service application is adapted to generate the healthcare asset intelligence using the selected service component.

Certain embodiments of the present invention provide a method for providing healthcare asset intelligence including acquiring healthcare asset intelligence data from a data warehouse using at least one service component, processing the acquired healthcare asset intelligence data using the at least one service component in a service-oriented architecture, and generating the healthcare asset intelligence based at least in part on the processing of the acquired healthcare asset intelligence data using service-oriented computing.

Certain embodiments of the present invention provide a computer-readable medium including a set of instructions for execution on a computer including a data acquisition routine, a processing routine, and an intelligence generation routine. The data acquisition routine is configured to acquire healthcare asset intelligence data. The processing routine is configured to process the acquired healthcare asset intelligence data based at least in part on a service application using a service-oriented architecture. The intelligence generation routine is configured to generate healthcare asset intelligence based at least in part on the processing routine using service-oriented computing and the service-oriented architecture.

Figure 1:
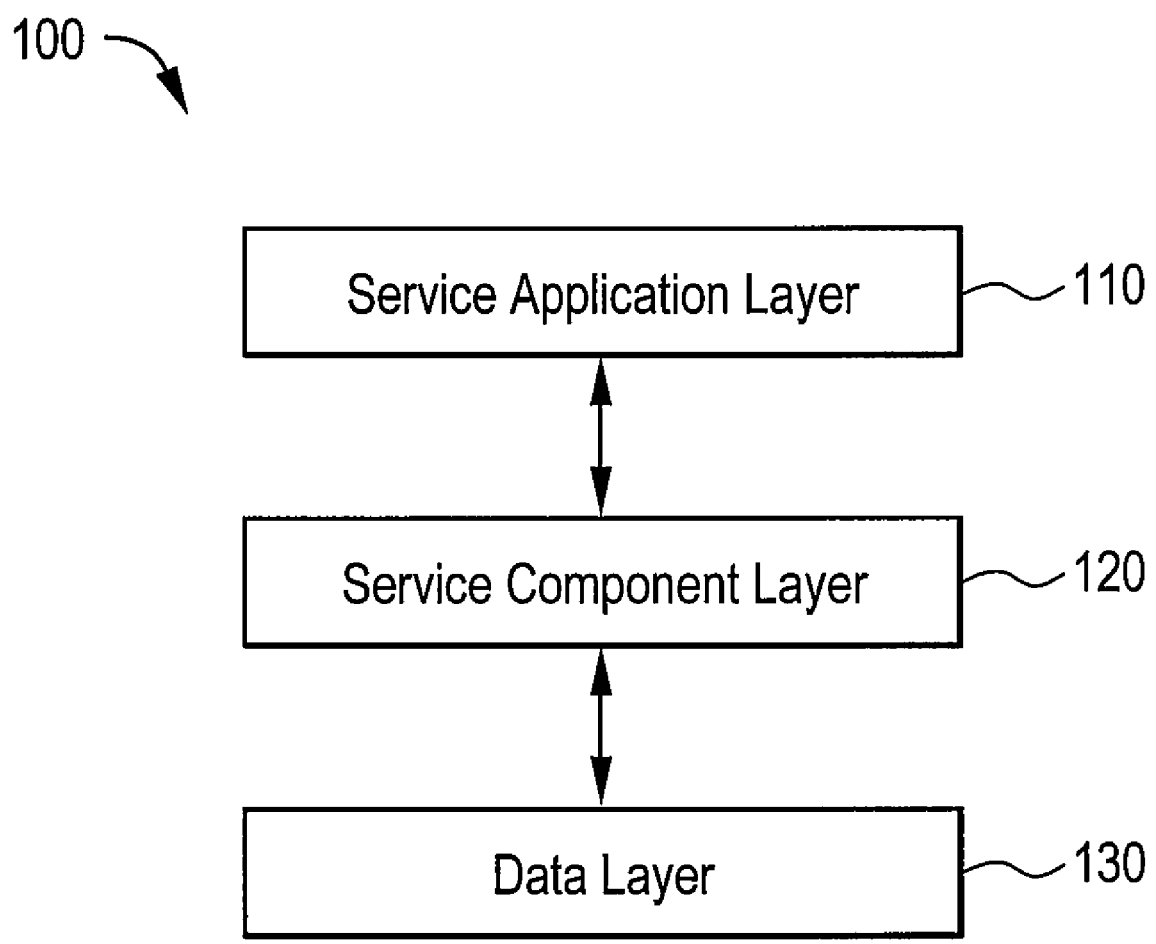
FIG. 1 illustrates a system for providing healthcare asset intelligence in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentalities shown in the attached drawings.

DETAILED DESCRIPTION OF THE INVENTION

Certain embodiments of the invention provide systems, methods, and/or apparatuses that may utilize data sets from different data sources in their existing format and provide the ability to construct service applications and/or decision-making applications using versatile service components in order to provide healthcare asset intelligence. The healthcare asset intelligence may include managing or making decisions concerning the healthcare assets in an enterprise. Moreover, certain embodiments provide an architecture that facilitates the rapid and inexpensive creation of service applications but still ensures the integrity of data being accessed by the service components of a given service application. Certain embodiments of the present invention are utilization-based, which may help enable the utilization of applications without guessing and/or estimating healthcare asset data.

Certain embodiments of the present invention provide architecture, methods, and processes for providing healthcare asset intelligence. Certain embodiments allow for optimal utilization of healthcare assets and/or scheduling of the healthcare assets based on asset utilization. Certain embodiments allow for a comparison of asset utilizations between different enterprise sub-groups (e.g., fleet level groups), such as a hospital or department. Certain embodiments of the present invention provide visibility of all the healthcare assets at an enterprise level. Certain embodiments provide a method to dynamically allocate assets among competing departments of a single hospital or an industry, or competing hospitals in a healthcare system. Certain embodiments of the present invention provide decision making applications for a healthcare enterprise using location data concerning the location of one or more data sources in the healthcare enterprise.

FIG. 1 illustrates a system 100 for providing healthcare asset intelligence in accordance with an embodiment of the present invention. The system 100 includes a service application layer 110, a service component layer 120, and a data layer 130.

The service application layer 110 is in communication with the service component layer 120. Additionally, the service component layer 120 is in communication with the data layer 130.

In operation, the system 100 is configured according to a service-oriented architecture and uses service-oriented computing. The data layer 130 preprocesses healthcare asset intelligence data. The service component layer 120 includes a plurality of service components, wherein each of the plurality of service components utilizes the healthcare asset intelligence data. The service application layer 110 includes a service application that utilizes at least one of the plurality of service components to provide healthcare asset intelligence.

An enterprise may implement system 100. The enterprise may be a healthcare provider or a group of healthcare providers, such as a hospital or a group of hospitals, for example.

In certain embodiments, the system 100 provides the healthcare asset intelligence by acquiring and processing the healthcare asset intelligence data. The healthcare asset intelligence may include information on healthcare asset utilization, healthcare asset forecasting, healthcare asset allocation and reallocation, and/or healthcare asset management, for example. The healthcare assets may include, for example, healthcare personnel, doctors, nurses, IV pumps, wheel chairs, patient beds, operating rooms, emergency rooms, imaging machines, surgical implements, medications, blood, saline, and other biomedical or healthcare equipment, supplies, or personnel.

The healthcare asset intelligence data may include information that may be useful in generating the healthcare asset intelligence, such as deciding how to manage healthcare assets. Information that may be useful in managing those assets may relate to demand for, access to, and use of the healthcare assets in an enterprise, for example. The healthcare asset intelligence may include decision support information such as a recommendation that additional IV pumps should be acquired in order to meet demand for the devices. The healthcare asset intelligence data includes any data that may be relevant in providing healthcare asset intelligence. For example, healthcare asset intelligence data may include the number of IV pumps currently available for use within an enterprise or the number of current hospital patients who require use of an IV pump.

In certain embodiments, the service application layer 110 functions independently from the service component layer 120. Thus, a change in the service component layer 120 may not impact the service application layer 110. The system 100 may also be configured so that the service component layer 120 functions independently from the data layer 130. Thus, a change in the data layer 130 may not impact the service component layer 120. The service application layer 110, the service component layer 120, and the data layer 130 are all described further below.

In certain embodiments, the independence of the service application layer 110, the service component layer 120, and the data layer 130 may help enable managing data in the data layer 130 without impacting the service application layer 110 and the service component layer 120, and changing the service component layer 120 without impacting the service application layer 110.

As described above, the system 100 is configured according to a service-oriented architecture (SOA) and uses service-oriented computing (SOC). SOAs and SOC are known in the art. SOAs generally separate functions into distinct services that may be distributed over a network and may be combined with one another to create applications. SOAs may allow a requester of services to choose a set of services to create an application that uses the selected services and to access the services using remote procedure calls, such as those developed by Xerox. The SOA may reduce the complexity of application development by maximizing loose coupling and the reuse of service components and existing code. SOC may enhance the offerings of SOA by allowing parties interacting through an SOA to apply their own local policies autonomously, while providing service management, service composition and orchestration, and service transaction management. The SOC may improve service transaction management and service composition.

The SOC and SOA may lend themselves to data mining applications; provide a data refresh rate suitable for data mining; support organization of healthcare asset intelligence data around subjects such as assets, patients, and/or others; provide a simple and concise view around the subjects while only utilizing and/or keeping relevant healthcare asset intelligence data for decision making; and support integration of healthcare asset intelligence data from multiple heterogeneous sources of the data, such as relational databases, hierarchical databases, flat files, and/or transactional records, as may be seen in a hospital environment, for example. The SOC and SOA may allow for data cleaning, data integration, and data preprocessing techniques to be applied to the integrated data sources. The SOC and SOA may be time variant and may support a separate data store from the operation environment which is non-volatile.

The system 100 may be created using existing data sources, which may comprise the data layer, and existing service components, which may comprise the service component layer. The existing service components may be selected and/or integrated for a particular service application. The service application may query one or more of the existing service components for information related to healthcare asset intelligence, for example.

A user of the system 100 may be an enterprise or hospital employee with administrative or management responsibilities, such as a chief executive officer, a chief financial officer, a head of a medical department, a chief resident, and/or a chief nurse, for example. In certain embodiments, the user may be an employee of a healthcare provider.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 2:
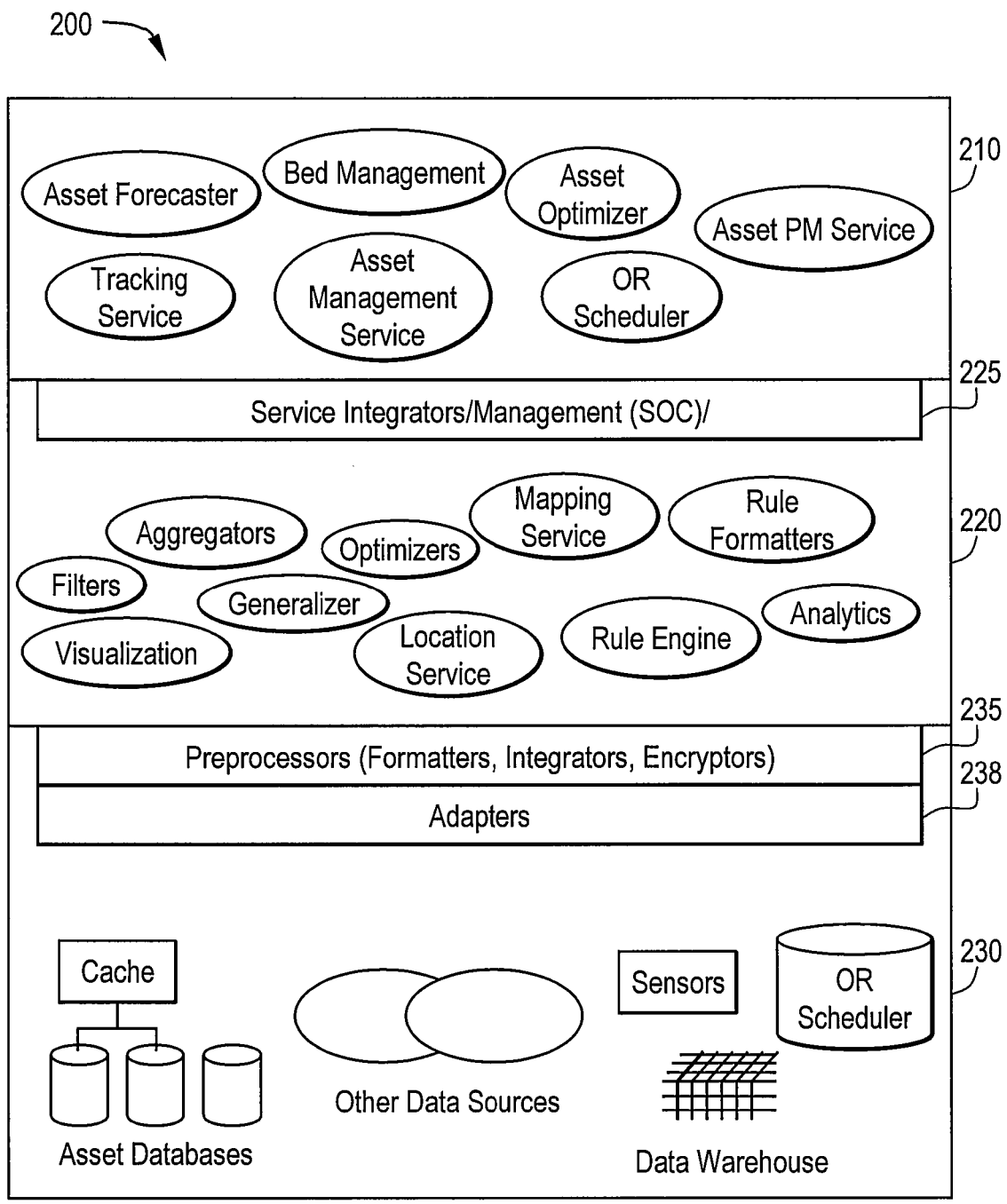
FIG. 2 illustrates a system for providing healthcare asset intelligence in accordance with an embodiment of the present invention.

FIG. 2 illustrates a system 200 for providing healthcare asset intelligence in accordance with an embodiment of the present invention. The system 200 includes a service application layer 210, a service component layer 220, and a data layer 230. The service component layer 220 includes one or more service integrators 225. The data layer 230 includes one or more preprocessors 235 and adapters 238. In certain embodiments, the system 200 is organized according to a service-oriented architecture (SOA) and uses service-oriented computing (SOC).

The service application layer 210 may be similar to the service application layer 110. The service component layer 220 may be similar to the service component layer 120. The data layer 230 may be similar to the data layer 130.

The service application layer 210 is in communication with the service component layer 220. The service component layer 220 is in communication with the data layer 230.

In operation, the data layer 230 preprocesses healthcare asset intelligence data. The service component layer 220 includes a plurality of service components, wherein each of the plurality of service components utilizes the healthcare asset intelligence data. The service application layer 210 includes a service application that utilizes at least one of the plurality of service components to provide healthcare asset intelligence.

In certain embodiments, the data layer 230 includes a variety of data sources. As shown in FIG. 2, the data layer 230 may include, for example, data sources such as sensors, schedulers, asset databases, a database cache, other databases, a data warehouse, and/or other data sources.

A sensor may be, for example, an RFID sensor capable of detecting the location of healthcare assets in the enterprise, a GPS receiver, a barcode scanner capable of scanning bar codes on healthcare assets, cameras capable of capturing images of healthcare assets, motion sensors capable of detecting motion in a room, such as an operating room, environment sensors, preparation status of a room, and other sensor capable of capturing information related to healthcare asset intelligence.

A scheduler may include data such as information about availability of an operating room, an emergency room, a patient bed, an imaging machine, or a hospital staff member, for example.

An asset database may include information about the healthcare assets, such as information about the number of hospital beds within a particular hospital, for example.

The database cache may store data originating from a multitude of data sources so that the stored data may be accessed quickly.

The data warehouse may allow for implementation of faster and more efficient data mining algorithms. The data warehouse may be created by integrating multiple data sources that may be located remotely from one another. The data warehouse may be configured so that some or all of the data stored within the warehouse is organized according to one or more clustering factors. For example, a clustering factor may call for the grouping of data for hospitals in the enterprise of a certain size, such as data relating to the assets of hospitals having fewer than one hundred patient rooms. As another example, a clustering factor may call for the grouping of data for all members of an enterprise which provide the same service, such as nursing home facilities, cardiovascular surgery facilities, or obstetrics facilities, for example. By using clustering factors to organize healthcare asset intelligence data, the data warehouse provides the ability to compare data between different members of a peer group of healthcare environments.

The data warehouse may update the healthcare asset intelligence data at various intervals. For example, the data warehouse may be updated one or more times per day. In certain embodiments, one of the service components may prompt the data warehouse to update the healthcare asset intelligence data.

By aggregating the healthcare asset intelligence data in the data warehouse, data retrieval time may be significantly decreased. For example, reports may be ready from the data warehouse as soon as it is updated.

Other databases or data sources within the data layer 230 may include, for example, information not directly related to a particular asset within the healthcare environment, such as data relating to the spread of a disease X. Although not necessarily directly related to an asset itself, such information may be useful in the event of an outbreak of disease X. For example, the database may include information relating to which assets, patients, or staff members came into contact with a patient with disease X. A user of the system 200 may wish to manage the healthcare assets differently if the outbreak were occurring.

In certain embodiments, the data layer 230 preprocesses and/or adapts the healthcare asset intelligence data. The preprocessors 235 may preprocess the healthcare asset intelligence data. The adapters 238 may adapt the healthcare asset intelligence data. The adapting and preprocessing may be performed either before or when a service component attempts to utilize the healthcare asset intelligence data, such as by reading or writing the healthcare asset intelligence data.

One or more of the adapters 238 may be used to access the data in the data layer 230 in various formats, or a particular data source within the data layer 230, by those of the service component layer 220, or a particular service component within the service component layer 220, to allow communication between them.

Because healthcare asset intelligence data may vary greatly in format, type, and security level, the data layer 230 may include the preprocessors 235 that provide formatting, integrating, and/or encrypting functionality in order to facilitate later processing of the healthcare asset intelligence data.

One or more of the preprocessors 235 may format the healthcare asset intelligence data. For example, the data layer 230 may provide access to the healthcare asset intelligence data in a common format, so that each service component may access, utilize, manipulate, and/or write the healthcare asset intelligence data in the same common format. The healthcare asset intelligence data may be stored in the data layer 230 in multiple different formats in the data sources. One or more of the preprocessors 235 may format the healthcare asset intelligence data into the common format, so that a service component may access the healthcare asset intelligence data. One or more of the preprocessors 235 may format the healthcare asset intelligence data into a format required by the data source in which the healthcare asset intelligence data is stored, so that a service component may write the healthcare asset intelligence data.

One or more of the preprocessors 235 may integrate the healthcare asset intelligence data. For example, the healthcare asset intelligence data may be stored in the data layer 230 in multiple different data sources that may be located remotely from one another. One or more of the preprocessors 235 may integrate the healthcare asset intelligence data stored in these different data sources, so that a service component may access the integrated healthcare asset intelligence data instead of having to access the healthcare asset intelligence data stored in each different data source.

One or more of the preprocessors 235 may encrypt the healthcare asset intelligence data. Encryption methods are known in the art and may utilize data substitution and/or transposition techniques, for example, to maintain data confidentiality and/or authenticate users. For example, Secure Sockets Layer (SSL) is an Internet-standard network encryption and authentication protocol that uses encryption to ensure data confidentiality and to authenticate users via digital certificates. In environments utilizing healthcare asset intelligence data, data confidentiality and user authentication may be particularly important. For example, the data layer 230 of the system 200 may include healthcare asset intelligence data that must be kept confidential, such as patient information that is subject to regulation by the Health Insurance Portability and Accountability Act (HIPAA). Healthcare asset intelligence data that must be kept confidential may include, for example, a patient's name, social security number, and/or health plan beneficiary number. This healthcare asset intelligence data may be included in, for example, a completed healthcare claim form, an explanation of benefits document, and/or an insurer's note that documents a discussion with a policyholder. In addition, authentication of a user may be required before that user is able to access data from or write data to the data layer 230. The user may be a hospital employee, such as nursing staff, for example.

In many healthcare environments, patients are identified so that each service component may access, utilize, manipulate, and/or write the healthcare asset intelligence data in the same common format.

In certain embodiments, the service components may access the data from the data layer 230 in raw format or through the preprocessors 235, adapters 238, or filters in the service component layer 220.

The service components may perform intelligent analysis on the healthcare asset intelligence data in order to, for example, intelligently manage assets, provide asset utilization reports, provide asset dashboards for asset location and status, provide asset planning/procurement, manage asset financial data, schedule assets among departments or participating hospitals in an enterprise.

In certain embodiments, one or more of the preprocessors 235 may be selectively employed. The preprocessors 235 may vertically or horizontally reduce of the data.

In certain embodiments, the service component layer 220 includes multiple distinct service components. For example, as shown in FIG. 2, the service component layer 220 may include an analytics component, a mapping service component, a rule formatter component, a rule engine component, a location service component, an optimizer component, a generalizer component, an aggregator component, a filter component, and a visualization component, among others.

The output of a service component may be a link or a file in XML, ASCII format, or any other formats, for example.

The analytics component may be adapted to process and/or analyze healthcare asset intelligence data. The analytics component may be similar to the data analytics unit 550 described in detail below with regard to FIG. 5. The analytics component may include a set of analysis modules that can take the data and process it based upon the need. The analysis may be for asset/patient/personnel management, identifying a location of a device, or characterizing the device or determining the health of the device or the patient using sensor data, for example. Each analysis module may consist of a set of input and output layers tailored to a specific type of analysis and an analysis engine performing the analysis. The analytics component may include the analysis engine. The input layer further filters the data before feeding it into the analysis engine and is helpful in mapping data into the right perspective for the type of analysis that needs to be performed. This module can exist either on a device (remote location) or in a back office at a centralized or distributed location. The output can be a link, or a file in XML, ASCII format, or any other format, for example. The analysis engine can be one of the following functions: Locate, Characterize, Alert/Inform, Billing, Asset Planning, Asset Procurement, Determination of asset end of life, Asset Scheduling, Asset Maintenance Schedule (Fixed or Usage-based), Contract, Inventory (requirement prediction, usage analysis), fleet analysis, repair/fix/correct/self heal, for example. These analysis engines are further discussed below, particularly with respect to FIG. 12.

The mapping service component may be adapted to translate data from one format and/or location to another. For example, the mapping service component may perform data mapping by using procedural code, by creating transforms, and/or by using graphical mapping tools. In certain embodiments, data mapping may be accomplished using data-driven mapping techniques. In certain embodiments, data mapping may be accomplished using semantic mapping techniques, for example, through the use of a metadata registry. Mapping may also include mapping of asset workflow stages, such as those shown in FIG. 14, to physical locations within the hospital.

The rule formatter component may be adapted to format and/or integrate one or more rules to be applied to the healthcare asset intelligence data acquired by the service component layer 220. Rules may exist in different formats within a hospital. For example, the emergency room may have a rule that if the number of IV pumps goes below 3, then a procurement process should be started. Pediatrics may have a rule that if the number of IV pumps goes below 1, then a procurement process should be started. These two rules may be in different formats. The rule formatter component may format the rules to the same format, such that the rule engine component may apply and/or process both rules.

The rule engine component may be adapted to apply a rule to the healthcare asset intelligence data acquired by the service component layer 220. The rule engine component may be similar to the rule engine 825 described in detail below with regard to FIG. 8.

The location service component may be adapted to acquire healthcare asset intelligence data relating to the location of an asset. For example, the location service component may acquire healthcare asset intelligence data indicating the locations of cardiac defibrillators in the enterprise from one or more RFID sensors within the data layer 230.

The optimizer component may be adapted to acquire healthcare asset intelligence data that may be used to optimize the use, acquisition, and/or management of healthcare assets. For example, the acquired healthcare asset intelligence relating to the distribution of medications within the hospitals of an enterprise may be compared or analyzed according to an established priority scheme in order to optimize the distribution of medication across the enterprise.

The generalizer component may be adapted to generalize specific healthcare asset intelligence data into a more simplified form. For example, the generalizer component may acquire healthcare asset intelligence data relating to the location of an MRI machine from the data layer 230 and/or the location service component. The acquired asset location data may be provided by, for example, a GPS receiver that is part of the data layer 230. The asset location data provided by the GPS receiver is likely to be very specific. However, if the user of the system 200 only wishes to identify which hospital within the enterprise currently houses the MRI machine, rather than the precise geographical location of the asset, then more generalized location information is sufficient. By generalizing the location of the MRI machine to merely the hospital currently housing the machine, the generalizer component is able to describe the MRI machine's location in an simplified manner that satisfies the user's inquiry without providing extraneous or unnecessary detail.

The aggregator component may be adapted to aggregate healthcare asset intelligence data from multiple and/or single data sources within the data layer 230. For example, the user of the system 200 may wish to identify the total number of X-ray scanners within a single enterprise containing 1,000 different hospitals. The aggregator component may acquire healthcare asset intelligence data indicating the number of X-ray scanners located within each of the 1,000 hospitals. This example acquisition results in a large amount of data originating from many different data sources. However, the aggregator component may aggregate this large amount of healthcare asset intelligence data into a summation that provides a service application with only the total number of X-ray scanners within the enterprise as a whole.

The filter component may be adapted to filter healthcare asset intelligence data acquired from the data layer 230. The filter component may perform data reduction by either horizontal or vertical reduction, generalization of lower level concepts to higher level, summarization of the data, or transforming to the higher level of concepts. The filter component may allow the reduction of data without losing much information entropy. The filter component may also provide abstraction to all the healthcare asset intelligence data in various formats by converting them into the common data format. This consistent format may prepare the data for easy and efficient analysis when needed.

For example, if only some subset of the acquired healthcare asset intelligence data is relevant to the healthcare asset intelligence sought by the user of the system 200, then the filtering component may filter out the unnecessary portions of the healthcare asset intelligence data and allow only the relevant subset to pass through the filter component.

The visualization component may visually display healthcare asset intelligence to the user of the system 200. For example, the user may wish to know how often a certain medication was prescribed across the enterprise during each month of the preceding year. The visualization component may acquire healthcare asset intelligence data relating to prescription statistics of the medication over the past year from the data layer 230. The visualization component may then translate this healthcare asset intelligence data into a bar graph with twelve bars, for example, wherein each bar represents the number of times the medication was described in a particular month during the preceding year.

A rental/usage report service component may use healthcare asset intelligence data related to rental data and provide rental/usage reports for each of the devices in the hospital. The reports may list the rented asset types by renter and/or provider. The reports may also list the amount an asset has been used and apply business rules and/or vender rules to help obtain available discounts from the vender, for example. By way of an example, a vender rule may be that monthly rental fees are not charged for wheelchairs used less than 5 days in a month. The rental data may include the rental company, date of rental, rental rates, and condition of rental, for example. The rental reports may provide the amount to be paid to each of the rental companies based at least in part on rate as well as rental rules, for example. This service component may also analyze the trend of the device usage in a department or in a hospital or in the whole enterprise and develop forecasts of future rental or purchase needs based at least in part on the usage trend.

An asset planning/procurement service component may be responsible for analyzing healthcare asset intelligence data relating to device usage data along with device maintenance and device configuration data to determine the useful life of the device. This may help in determining the need for devices, time to procure them, and time to retire them.

A financial service component may analyze the healthcare asset intelligence data relating to the financials associated with a device. The maintenance of this data is used for controlling the cost of the device. This service component may keep track of both static (information received during purchase) as well as dynamic (lease/rental, depreciation) data.

A device scheduler service component may be responsible for scheduling the devices based at least in part on availability, need, and optimal cost of assignment.

A service component within the service component layer 220 may be able to acquire healthcare asset intelligence data from the data layer 230 and write healthcare asset intelligence data to the data layer 230. In certain embodiments, the service component layer 220 is configured so that multiple service components are able to function in conjunction with one another. Where multiple service components are to be utilized in tandem to provide healthcare asset intelligence, one or more service integrators 225 may be used to integrate and manage the service components and/or the healthcare asset intelligence data they utilize.

In situations where multiple service components attempt to read data from or write data to the data layer 230, concerns of data integrity are presented. For example, if the quantity of a particular type of asset is continuously updated based at least in part on the current level of asset utilization and the business processes of the healthcare environment, then access to the data among multiple service components can be regulated to ensure its integrity. To allow multiple service components to access the data layer 230 and still maintain the healthcare asset intelligence data's integrity, the SOA of the system 200 is extended to utilize the SOC. By using SOC principles, transactions between the service component layer 220 and the data layer 230 may be managed in order to serialize access to the data layer 230 among multiple service components. For example, if two service components within the service component layer 220 wish to access the data layer 230 or a component thereof, each service component may be granted access only when it is that particular component's turn. By serializing access to the data layer 230 among multiple service components in accordance with SOC principles, the system 200 provides serial access to ensure data integrity. In certain embodiments, the SOC tools providing serial access may be a component of the service integrators 225, as shown in FIG. 2. In certain embodiments, the preprocessors 235 and/or adapters 238 may provide serial access.

In certain embodiments, the service application layer 210 includes multiple distinct service applications. For example, as shown in FIG. 2, the service application layer 210 may include a tracking service application, an asset forecaster application, an asset optimizer application, an asset management service application, a bed management application, an asset periodic maintenance service, and an operating room scheduler, among others. Each service application within the service application layer 210 is able to provide healthcare asset intelligence by utilizing one or more service components within the service component layer 220. For example, a given service application may require three distinct service components to work in conjunction with one another in order to provide healthcare asset intelligence.

In certain embodiments, the service components needed to run each service application are pre-determined so that when the user of the system 200 selects an application, the appropriate service components are automatically selected for use. In certain embodiments, the user of the system 200 may customize an existing service application or construct a new service application by adding or subtracting service components for use by the service application.

In certain embodiments, the components of the system 200 may be located remotely from one another or may be integrated at a centralized site. In certain embodiments, individual data sources within the data layer 230 may be located remotely from one another. Individual service components, any devices used to select between them or obtain their results, and/or any devices used to achieve the service components' functionality may be located remotely from one another.

In certain embodiments, the data layer 230, the service component layer 220, and the service application layer 210 are stored at a centralized site. This centralized site may be located, for example, in a back office of the service providing entity, at a centralized location in the enterprise, or at a particular location within a healthcare enterprise. For example, the back office may be the General Electric back office. Additionally, some embodiments contemplate using two or more systems 200 in conjunction with one another. For example, if two healthcare providers each maintain their own system 200 but wish to utilize one another's healthcare asset intelligence data, service components, or service applications, the systems 200 may be adapted to communicate with one another.

If the system 200 is only for a single hospital, the system may be installed on a local server. One or more generic service components can reside on a device, the centralized site, and/or the back office based at least in part on the location of the healthcare asset intelligence data. The location of the service components may depend on the proprietary nature of the analysis and the end user. Caching may maintain the effectiveness of a service application in spite of the distributed nature of the residence of service components and the healthcare asset intelligence data.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 3:
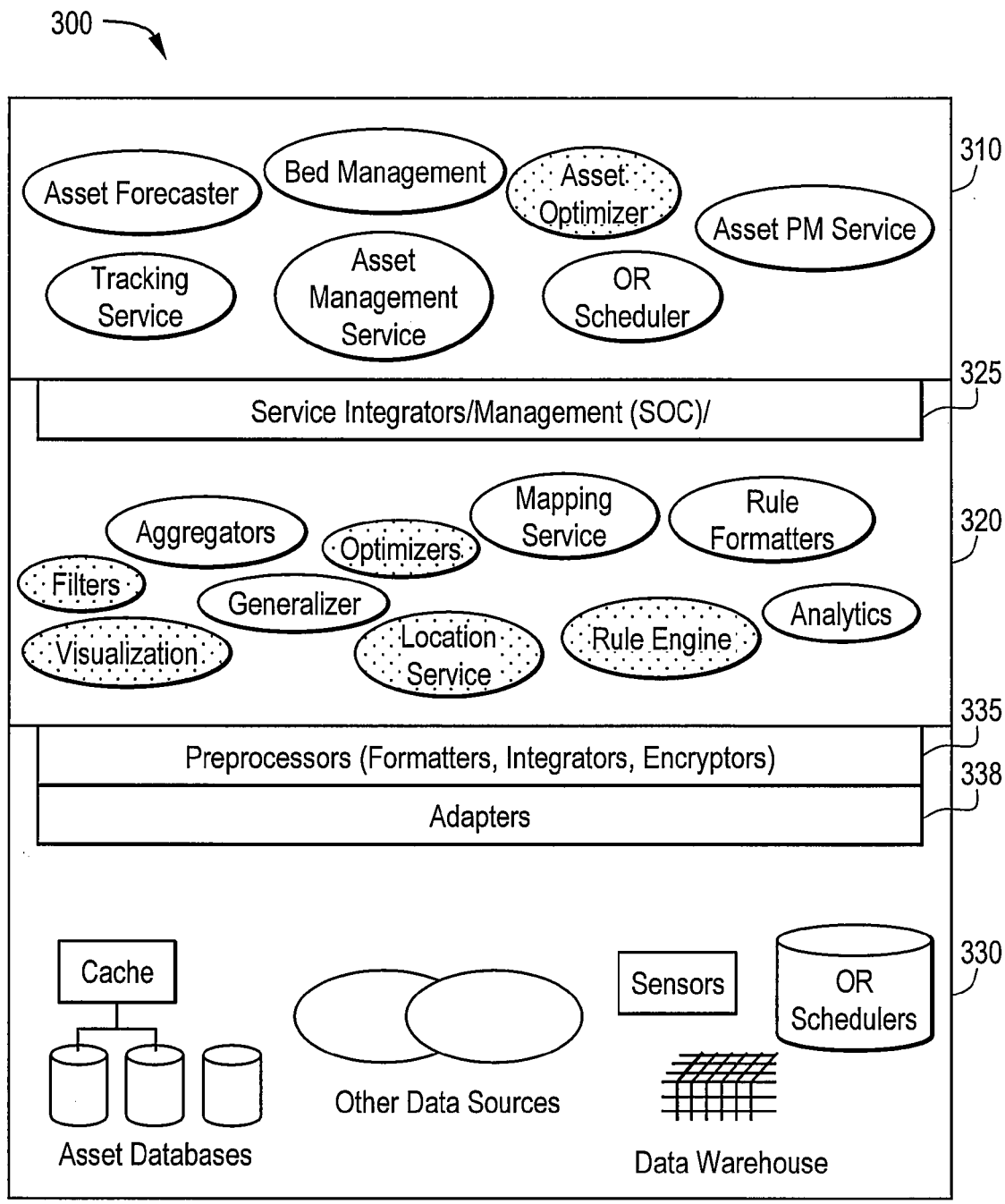
FIG. 3 illustrates a system for providing healthcare asset intelligence in accordance with an embodiment of the present invention.

FIG. 3 illustrates a system 300 for providing healthcare asset intelligence in accordance with an embodiment of the present invention. The system 300 includes a service application layer 310, a service component layer 320, and a data layer 330. The service component layer 320 includes one or more service integrators 325. The data layer 330 includes one or more preprocessors 335 and adapters 338. In operation, the system 300 is configured according to a service-oriented architecture (SOA) and uses service-oriented computing (SOC).

The system 300, the service application layer 310, the service component layer 320, the data layer 330, the one or more service integrators 325, the one or more preprocessors 335, and the one or more adapters 338 may be similar to the system 200, the service application layer 210, the service component layer 220, the data layer 230, the one or more service integrators 225, the one or more preprocessors 235, and the one or more adapters 238, respectively. The system 300 may be configured, for example, as described above with regard to the system 200 of FIG. 2.

The service application layer 310 is in communication with the service component layer 320. The service component layer 320 is in communication with the data layer 330.

The system 300 shown in FIG. 3 is an example embodiment of the system 200.

The service application layer 310 includes a service application called an asset optimizer application. The asset optimizer application has been selected, as indicated by the shading of that service application. The asset optimizer application uses five service components in combination: a filtering component, a visualization component, an optimizer component, a location service component, and a rule engine component. These service components are integrated by one or more of the service integrators 325. Additionally, in certain embodiments, the ability of each service component to access the data layer 330 may be regulated by one or more of the service integrators 325, which may provide serial access in accordance with SOC principles. In certain embodiments, the adapters 338 and/or preprocessors 335 may regulate the service components so that only serial access to the data layer 330 is available. Before the healthcare asset intelligence data is acquired by the service component layer 320, the adapters 338 and the preprocessors 335 may ensure that the healthcare asset intelligence data is properly formatted, integrated, and/or encrypted when the healthcare asset intelligence data is communicated between the service component layer 320 and the data layer 330.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 4:
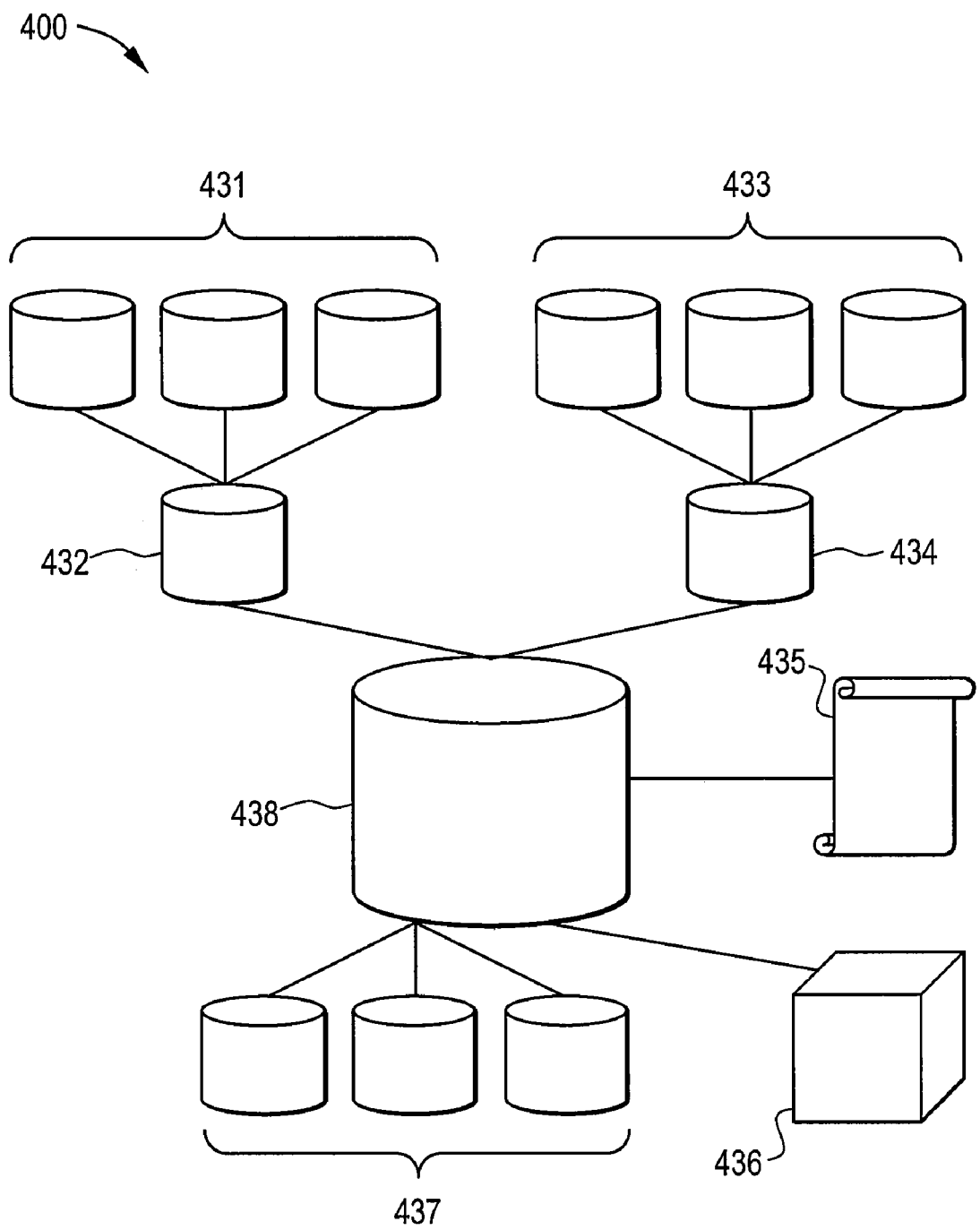
FIG. 4 illustrates a data storage environment for providing healthcare asset intelligence in accordance with an embodiment of the present invention.

FIG. 4 illustrates a data storage environment 400 for providing healthcare asset intelligence in accordance with an embodiment of the present invention. The data storage environment 400 includes a first set of data sources 431, a first integrated data source 432, a second set of data sources 433, a second integrated data source 434, a flat files source 435, a transactional data source 436, a set of data archivals 437, and a data warehouse 438. The data storage environment 400 may be similar to the data warehouse described above with regard to the data layer 230 of FIG. 2.

The first set of data sources 431 is in communication with the first integrated data source 432. The second set of data sources 433 is in communication with the second integrated data source 434. The data warehouse 438 is in communication with the first integrated data source 432, the second integrated data source 434, the flat files source 435, the transactional data source 436, and the set of data archivals 437.

In operation, the data warehouse 438 stores healthcare asset intelligence data from one or more of the first integrated data source 432, the second integrated data source 434, the flat files source 435, the transactional data source 436, and the set of data archivals 437. The first integrated data source 432 integrates the healthcare asset intelligence data stored in each unit of the first set of data sources 431. The second integrated data source 434 integrates the healthcare asset intelligence data stored in each emit of the second set of data sources 433. The data warehouse 438 may include more data sources than those comprising the first set of data sources 431 and the second set of data sources 433. The data storage environment 400 may also include more integrated data sources than those comprising the first integrated data source 432 and the second integrated data source 434. The data warehouse 438 integrates the healthcare asset intelligence data stored within the other components of the data storage environment 400 for use at an enterprise level. The data warehouse 438 may integrate, aggregate, and/or filter the healthcare asset intelligence data stored in a data layer, such as the data layer 230 or 330.

The data warehouse 438 retrieves healthcare asset intelligence data from and may write the healthcare asset intelligence data to one or more data sources, such as the first integrated data source 432, the second integrated data source 434, the flat files source 435, the transactional data source 436, and/or the set of data archivals 437. For example, if healthcare asset intelligence data is retrieved from the data warehouse 438 and later written back to the data warehouse 438 by the service component layer, the data warehouse 438 may also update the healthcare asset intelligence data stored in the data sources. The service component layer may be similar to the service component layer described above in reference to FIGS. 1, 2, and 3.

The flat files source 435 may include records such as, for example, name-and-address listings.

The transactional data source 436 may include data that describes events or exchanges such as, for example, invoices and activity records.

The set of data archivals 437 may include historical data, for example.

In certain embodiments, the first integrated data source 432 and the second integrated data source 434 may be located remotely from one another and/or in the same network. In addition, one or more of the units comprising the first set of data sources 431 or the second set of data sources 433 may be located remotely from one another. In certain embodiments, the data warehouse 438 is part of a centralized site that may be located, for example, in a back office or at a particular location within an enterprise. In certain embodiments, the data storage environment 400 may also include relational databases and/or hierarchical databases.

In certain embodiments, the data warehouse 438 may be in communication with a plurality of integrated data sources which are each in communication with one or more data sources.

In certain embodiments, the data warehouse 438 may be structured around a service application. In certain embodiments, an integrated data source, such as the integrated data sources 432 and 434, may be structured around a department in an enterprise. In certain embodiments individual data sources, such as the data sources in the first set of data sources 431 and the second set of data sources 432, may each be individually structured.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 5:
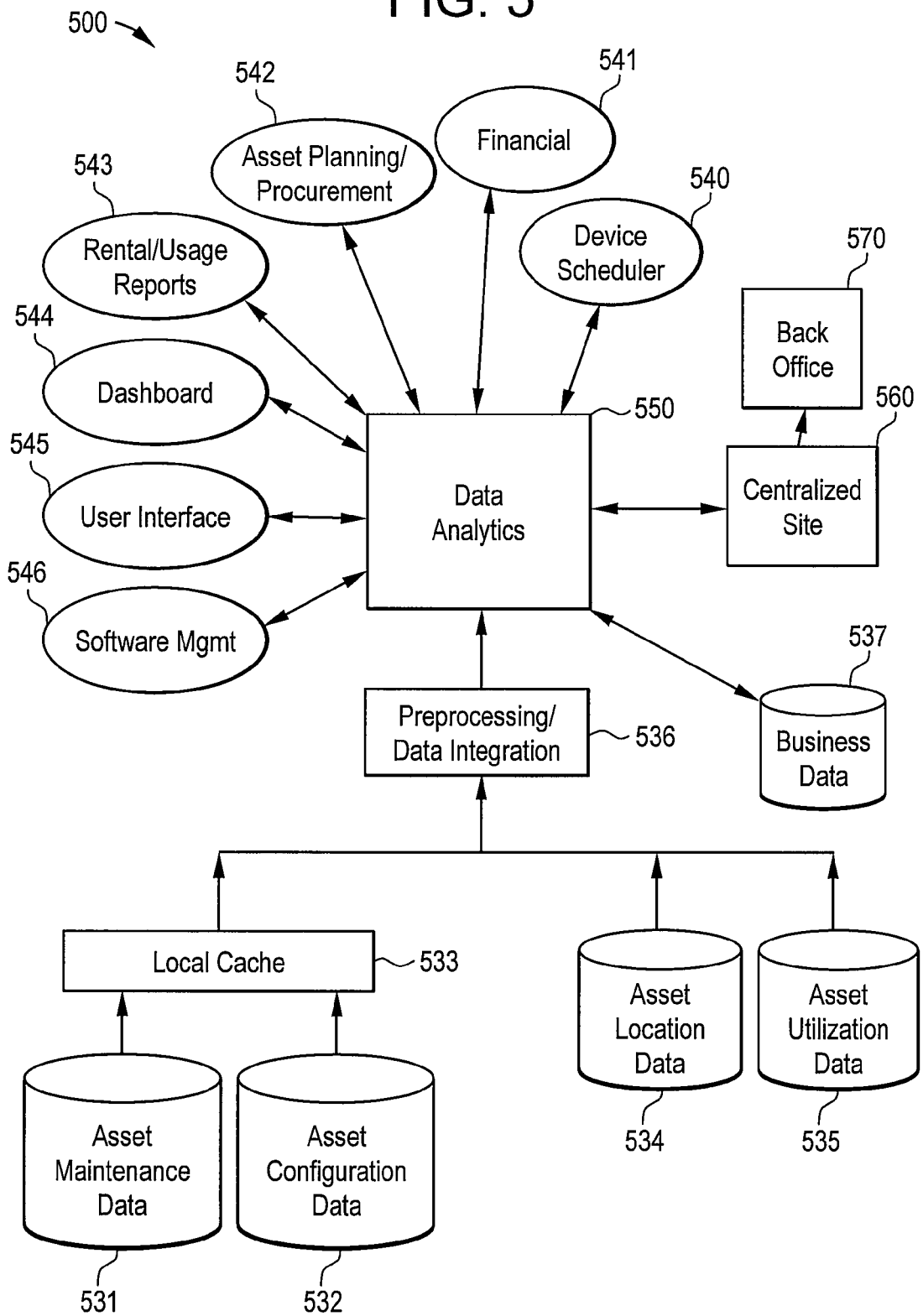
FIG. 5 illustrates a system for providing healthcare asset intelligence in accordance with an embodiment of the present invention.

FIG. 5 illustrates a system 500 for providing healthcare asset intelligence in accordance with an embodiment of the present invention. The system 500 includes an asset maintenance data source 531, an asset configuration data source 532, a local cache 533, an asset location data source 534, an asset utilization data source 535, a preprocessor unit 536, a business data source 537, a device scheduler 540, a financial unit 541, an asset planning unit 542, a rental/usage report unit 543, a dashboard 544, a user interface 545, a software management unit 546, a data analytics unit 550, a centralized site 560, and a back office 570.

The data analytics unit 550 is in communication with the preprocessor unit 536, the business data source 537, the device scheduler 540, the financial unit 541, the asset planning unit 542, the rental/usage report unit 543, the dashboard 544, the user interface 545, the software management unit 546, and the centralized site 560. The centralized site 560 is in communication with the back office 570. The asset maintenance data source 531 and the asset configuration data source 532 are in communication with the local cache 533. The preprocessor unit 536 is in communication with the local cache 533, the asset location data source 534, and the asset utilization data source 535.

The system 500 may be similar to the systems 200 and 300. The preprocessor unit 536 may be similar to the preprocessors 235 and 335. The data analytics unit 550 may be similar to the analytics component described above with regard to FIGS. 2 and 3. The centralized site 560 may be similar to the centralized site discussed above in reference to FIGS. 2 and 4. The back office 570 may be similar to the back off ice discussed above in reference to FIGS. 2 and 4.

In operation, the data analytics unit 550 provides healthcare asset intelligence, such as information relevant to asset management within a healthcare environment, to the centralized site 560. The healthcare asset intelligence developed by the data analytics unit 550 may be derived from healthcare asset intelligence data provided by the preprocessor unit 536, the business data source 537, the device scheduler 540, the financial unit 541, the asset planning unit 542, and/or the rental/usage report unit 543. The healthcare asset intelligence data provided by the preprocessor unit 536 may be derived from the asset maintenance data source 531, the asset configuration data source 532, the asset location data source 534, and/or the asset utilization data source 535. The preprocessor unit 536 may be configured, for example, as described above with regard to the preprocessors 235 of FIG. 2. The centralized site 560 may provide the healthcare asset intelligence directly to the back office 570 or perform additional processing of the healthcare asset intelligence before providing it to the back office 570. In certain embodiments, a user of the system 500 may interact with the data analytics unit 550 using the dashboard 544 and/or the user interface 545. In certain embodiments, the system 500 is used in an enterprise, in which the back office 570 of the enterprise maintains complete asset visibility among all the individual branches of the enterprise. This configuration may allow for dynamic asset allocation and optimal asset utilization throughout the enterprise. In certain embodiments, healthcare asset intelligence data may be acquired from the centralized site 560 by the data analytics unit 550.

The asset maintenance data source 531 may include data relating to the maintenance of an asset, such as when maintenance was most recently preformed on the asset, what maintenance was performed, and/or the next time for which maintenance of the asset is scheduled.

The asset configuration data source 532 may include data relating to the configuration of an asset. For example, the asset configuration data source 532 may include operating instructions and/or specifications for an X-ray scanner.

The local cache 533 may store data originating from the asset maintenance data source 531 and the asset configuration data source 532, so that the stored data may be accessed quickly.

The asset location data source 534 may include data relating to the location of an asset. For example, the asset location data source 534 may include the location of an MRI machine within a hospital. The asset location data source 534 may also include other data which may be aggregated together with the location data, such as the location of patients scheduled to use the MRI machine, for example.

The asset utilization data source 535 may include data relating to the utilization of an asset. For example, the asset utilization data source 535 may include the percentage of hospital beds within a hospital that are currently occupied by patients.

The business data source 537 may include, for example, data such as the annual operating budget for a hospital or enterprise.

The device scheduler 540 may schedule an asset, such as a hospital operating room, based at least in part on factors such as the number of requests to be accommodated, the availability of the asset, and the minimization of financial costs.

The financial unit 541 may be adapted to provide data associated with the financials of an asset. In certain embodiments, the financial unit 541 provides and/or analyzes both static (e.g., information received during purchase) as well as dynamic (e.g., lease/rental, depreciation) financial data associated with the asset.

The asset planning unit 542 may be adapted to analyze data associated with the usage, maintenance, and/or configuration of an asset. In certain embodiments, this analysis allows the asset planning unit 542 to determine the useful life of the asset.

The rental/usage report unit 543 may be adapted to analyze data associated with the rental of an asset and provide a rental/usage report of the asset. The rental data may include, for example, the rental company, the date of rental, the applicable rental rates, and the conditions of the rental. The rental/usage report may include, for example, the amount to be paid to the rental company based at least in part on the rates and conditions of the rental. In certain embodiments, the rental/usage report unit 543 may also analyze the trend of the asset's usage within a department, hospital, and/or enterprise and develop forecasts of future rental or purchase needs based at least in part on the usage trend.

The dashboard 544 may provide an asset's location and status. For example, the dashboard 544 may comprise an instrument panel or control panel that allows the user of the system 500 to view the status of an asset.

The user interface 545 may allow the user of the system 500 to interact with one or more elements of the system 500. For example, the user interface 545 may include a keyboard, a touch screen, a mouse, a joystick, a button, a knob, a voice recognition unit, an optical scanner, and/or some other means for facilitating interaction between the user and the system 500.

The software management unit 546 may regulate the software utilized by the system 500 for acquiring and processing healthcare asset intelligence data. In certain embodiments, the software management unit 546 operates automatically without the need for a user's intervention. In certain embodiments, the user may communicate with the software management unit 546 in order to regulate the functionality of the system 500 or any of its components.

The centralized site 560 may be a location at which healthcare asset intelligence data is stored and/or processed. For example, the centralized site may be a particular location within a hospital or enterprise. The centralized site 560 may comprise a storage unit, a processing unit, and/or an output unit. The centralized site 560 may enable an enterprise-wide solution to certain asset management problems. The centralized site 560 may be within a hospital system, as compared to the back office 570 of a provider of the system 500. The centralized site 560 allows for data from multiple different departments, hospitals, and/or healthcare service providers in an enterprise to be analyzed and compared.

The back office 570 may be a location at which healthcare asset intelligence data is stored and/or processed. The back office 570 may comprise one or more servers which may each comprise a storage unit, a processing unit, and/or an output unit. Healthcare asset intelligence data stored in the back office 570 may be used for analysis at an enterprise sub-group level, such as a fleet level. By storing the healthcare asset intelligence data in the back office 570, the data may be stored according to a clustering factor as discussed above. The back office 570 may be a back office of a provider of the system 500, for example, such as General Electric. In certain embodiments, the back office may store one or more components and/or layers of the system 500. In certain embodiments, the back office 570 may store aggregated, generalized, and/or filtered relevant healthcare asset intelligence data for all hospitals in an enterprise. The data stored in the back office 570 may be used to segment/cluster the hospitals based at least in part on asset usage by each hospital. Already existing clustering of hospitals based at least in part on procedures (type, complexity, number) performed by the hospitals may be utilized for proposing optimal utilization of assets to a hospital in a cluster where the asset utilization may have been higher.

In certain embodiments, the back office 570 may support a fleet level analytic or analysis service component to analyze consumption of assets for future business growth.

Using the three-layer architecture described above in FIGS. 1, 2, and 3, the components of the system 500 may be divided between the centralized site 560, the back office 570, and/or one or more servers in the enterprise.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 6:
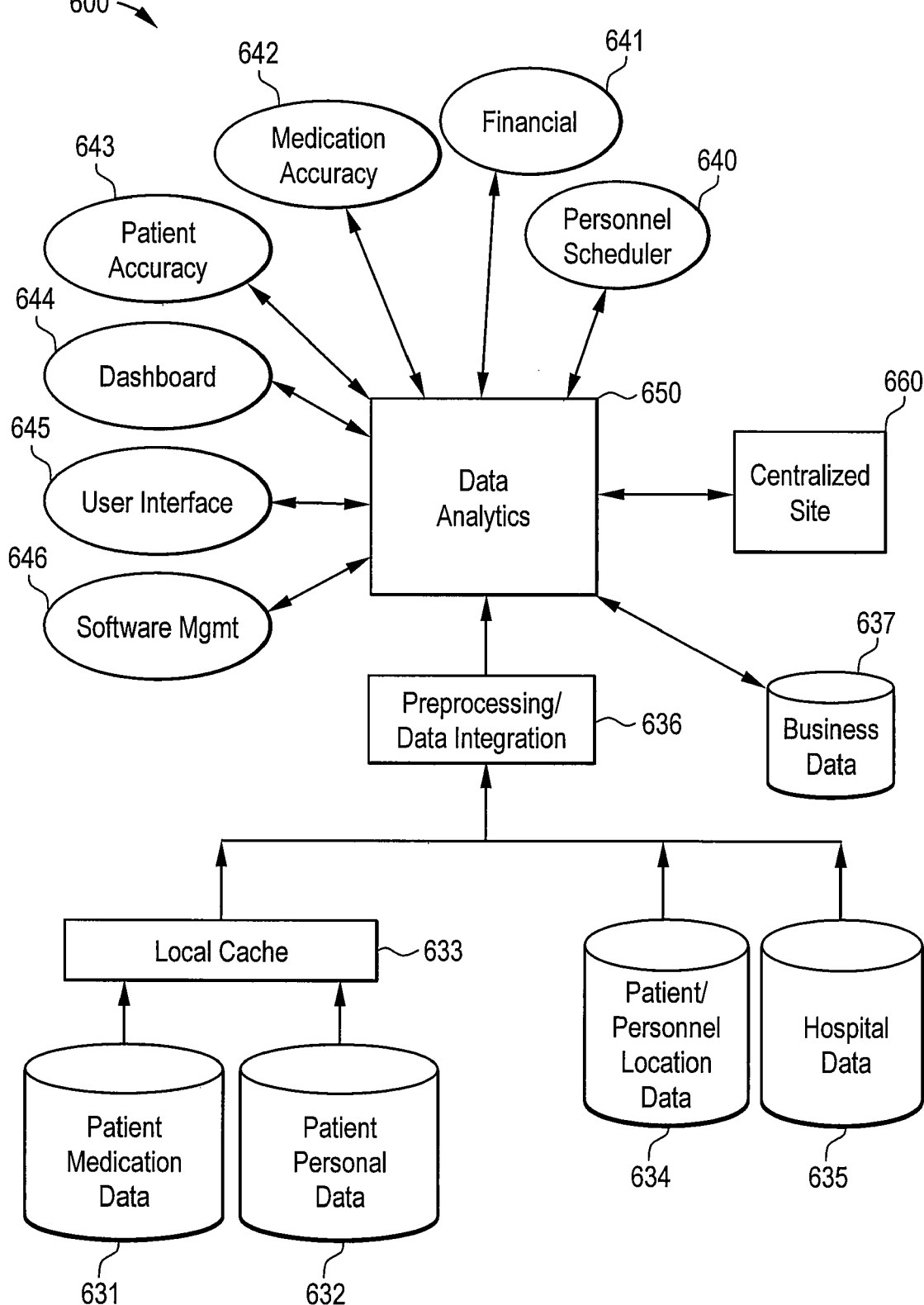
FIG. 6 illustrates a system for providing healthcare asset intelligence in accordance with an embodiment of the present invention.

FIG. 6 illustrates a system 600 for providing healthcare asset intelligence in accordance with an embodiment of the present invention. The system 600 includes a patient medication data source 631, a patient personal data source 632, a local cache 633, a patient/personnel location data source 634, a hospital data source 635, a preprocessor unit 636, a business data source 637, a personnel scheduler 640, a financial unit 641, a medication accuracy verifier 642, a patient accuracy verifier 643, a dashboard 644, a user interface 645, a software management unit 646, a data analytics unit 650, and a centralized site 660.

The data analytics unit 650 is in communication with the preprocessor unit 636, the business data source 637, the personnel scheduler 640, the financial unit 641, the medication accuracy verifier 642, the patient accuracy verifier 643, the dashboard 644, the user interface 645, the software management unit 646, and the centralized site 660. The patient medication data source 631 and the patient personal data source 632 are in communication with the local cache 633. The preprocessor unit 636 is in communication with the local cache 633, the patient/personnel location data source 634, and the hospital data source 635.

The system 600 may be similar to the systems 200, 300, and 500. The preprocessor unit 636 may be similar to the preprocessors 235 and 335 and the preprocessor unit 536. The data analytics unit 650 may be similar to the analytics component described above with regard to FIGS. 2 and 3, as well as the data analytics unit 550. The local cache 633, the business data source 637, the financial unit 641, the dashboard 644, the user interface 645, the software management unit 646, and the centralized site 660 may be similar to the local cache 533, the business data source 537, the financial unit 541, the dashboard 544, the user interface 545, the software management unit 546, and the centralized site 560, respectively.

In operation, the data analytics unit 650 provides the healthcare asset intelligence, such as information relevant to asset management within a healthcare environment, to the centralized site 660. The healthcare asset intelligence developed by the data analytics unit 650 is derived from healthcare asset intelligence data provided by the preprocessor unit 636, the business data source 637, the personnel scheduler 640, the financial unit 641, the medication accuracy verifier 642, and/or the patient accuracy verifier 643. The healthcare asset intelligence data provided by the preprocessor unit 636 is derived from the patient medication data source 631, the patient personal data source 632, the patient/personnel location data source 634, and the hospital data source 635. The preprocessor unit 636 may be configured, for example, as described above with regard to the preprocessors 235 of FIG. 2 or the preprocessor unit 536. In certain embodiments, a user of the system 600 may interact with the data analytics unit 650 using the dashboard 644 and/or the user interface 645. In certain embodiments, the system 600 is used in an enterprise. In certain embodiments, healthcare asset intelligence data may be acquired from the centralized site 660 by the data analytics unit 650.

The patient medication data source 631 may include data relating to, for example, a patient's list of current medications or medication history.

The patient personal data source 632 may include, for example, a patient's contact and/or demographic information.

The patient/personnel location data source 634 may include location data such as the current location of a patient or a hospital staff member.

The hospital data source 635 may include, for example, general information about a hospital, such as the regular hours of operation of various departments within the hospital, the hospital's size, the hospital's location, and/or the hospital's financial and commercial data.

The personnel scheduler 640 may schedule personnel, such as doctors or nurses, based at least in part on factors such as the number of doctors or nurses currently on duty at a particular hospital, availability of additional doctors or nurses, and demand for doctors or nurses.

The medication accuracy verifier 642 may be adapted to track the amount of medication available, the amount of medication dispensed, and the amount of medication prescribed. In certain embodiments, the medication accuracy verifier 642 may be adapted to verify that a particular medication has been administered.

The patient accuracy verifier 643 may be adapted to analyze information about a patient, such as the patient's voice and/or fingerprint, to confirm the identity of the patient.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 7:
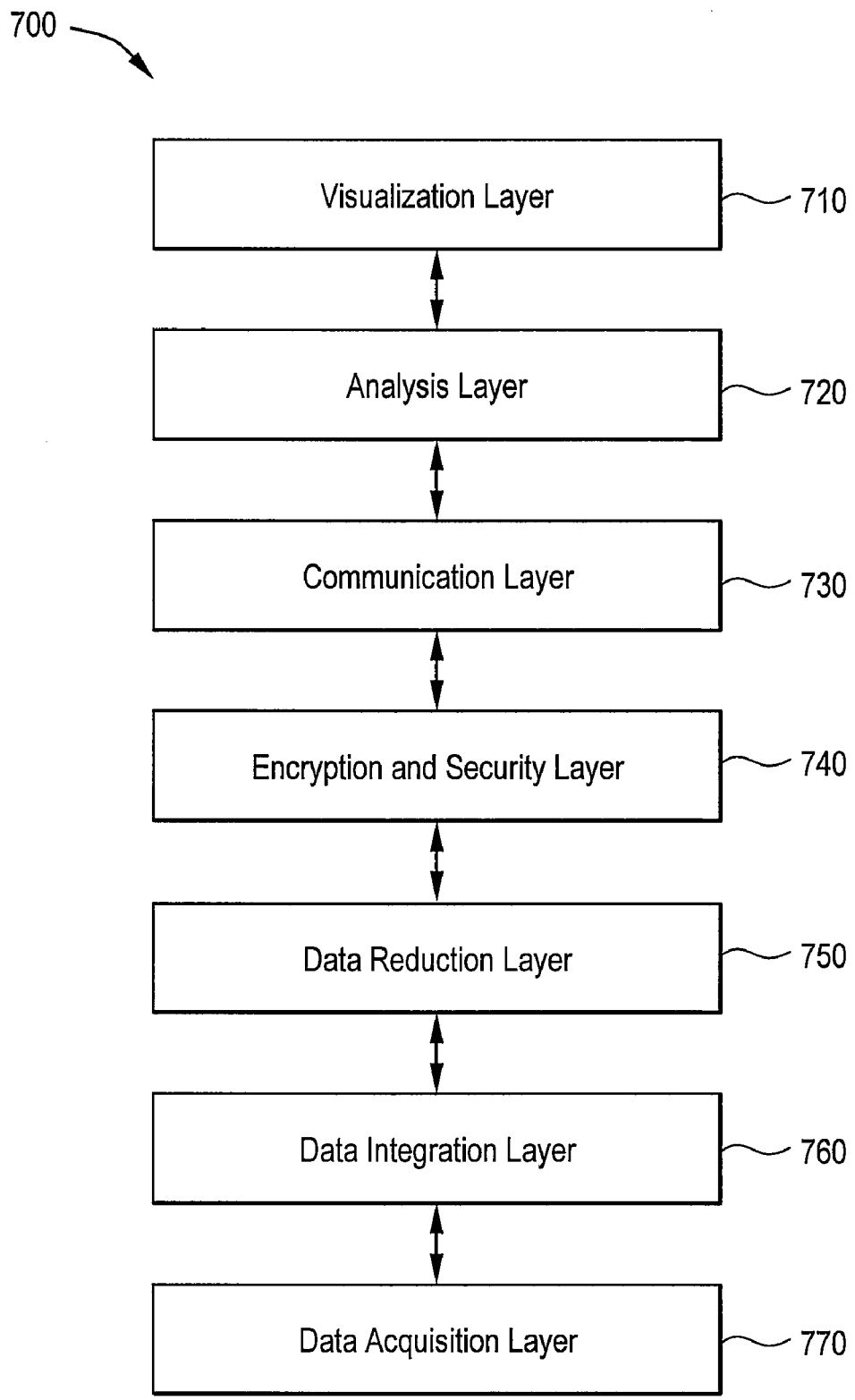
FIG. 7 illustrates a system for providing healthcare asset intelligence in accordance with an embodiment of the present invention.

FIG. 7 illustrates a system 700 for providing healthcare asset intelligence in accordance with an embodiment of the present invention. The system 700 includes a visualization layer 710, an analysis layer 720, a communication layer 730, an encryption and security layer 740, a data reduction layer 750, a data integration layer 760, and a data acquisition layer 770.

The analysis layer 720 is in communication with the visualization layer 710 and the communication layer 730. The encryption and security layer 740 is in communication with the communication layer 730 and the data reduction layer 750. The data integration layer 760 is in communication with the data reduction layer 750 and the data acquisition layer 770.

The system 700 may be similar to the systems 100, 200, 300, 500, and 600. The visualization layer 710 may be similar to the visualization components of the service component layers 220 and 320. The analysis layer 720 may be similar to the service component layers 120, 220, and 320. The encryption and security layer 740 may be similar to the preprocessors 235 and 335 and the preprocessor units 536 and 636. The data reduction layer 750 may be similar to the filter components of the service component layers 220 and 320, the preprocessors 235 and 335, and the preprocessor units 536 and 636. The data integration layer 760 may be similar to the preprocessors 235 and 335 and the preprocessor units 536 and 636. The data acquisition layer 770 may be similar to the data layers 130, 230, and 330.

In operation, the data acquisition layer 770 acquires healthcare asset intelligence data, which includes hospital data and patient data. This data is provided to and integrated by the data integration layer 760. The integrated healthcare asset intelligence data is provided to and filtered by the data reduction layer 750. The filtered healthcare asset intelligence data is encrypted or otherwise secured by the encryption and security layer 740. The encrypted healthcare asset intelligence data is provided to the communication layer 730, which provides the data to the analysis layer 720 for the performance of any necessary analysis. The analysis layer 720 analyzes the healthcare asset intelligence data to produce the healthcare asset intelligence. The healthcare asset intelligence is provided to the visualization layer 710, which may be configured to visually display the healthcare asset intelligence to a user of the system 700.

The data reduction layer 750 may perform data reduction by either horizontal or vertical reduction, generalization of lower level concepts to higher level, summarization of the data, or transforming to the higher level of concepts. The data reduction layer 750 may allow the reduction of data without losing much information entropy. The data reduction layer 750 may also provide abstraction to all the healthcare asset intelligence data in various formats by converting them into a common data format. This consistent format may prepare the data for easy and efficient analysis when needed.

In certain embodiments, one or more of the various layers of the system 700 may be reordered or omitted without affecting the overall functionality of the system 700. For example, the system 700 may be configured without the encryption and security layer 740. It may be unnecessary to include the encryption and security layer 740 if, for example, no confidential information is to be passed through the system 700. Despite the omission of this layer, the interaction of the remaining layers nonetheless allows the system 700 to provide the healthcare asset intelligence.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 8:
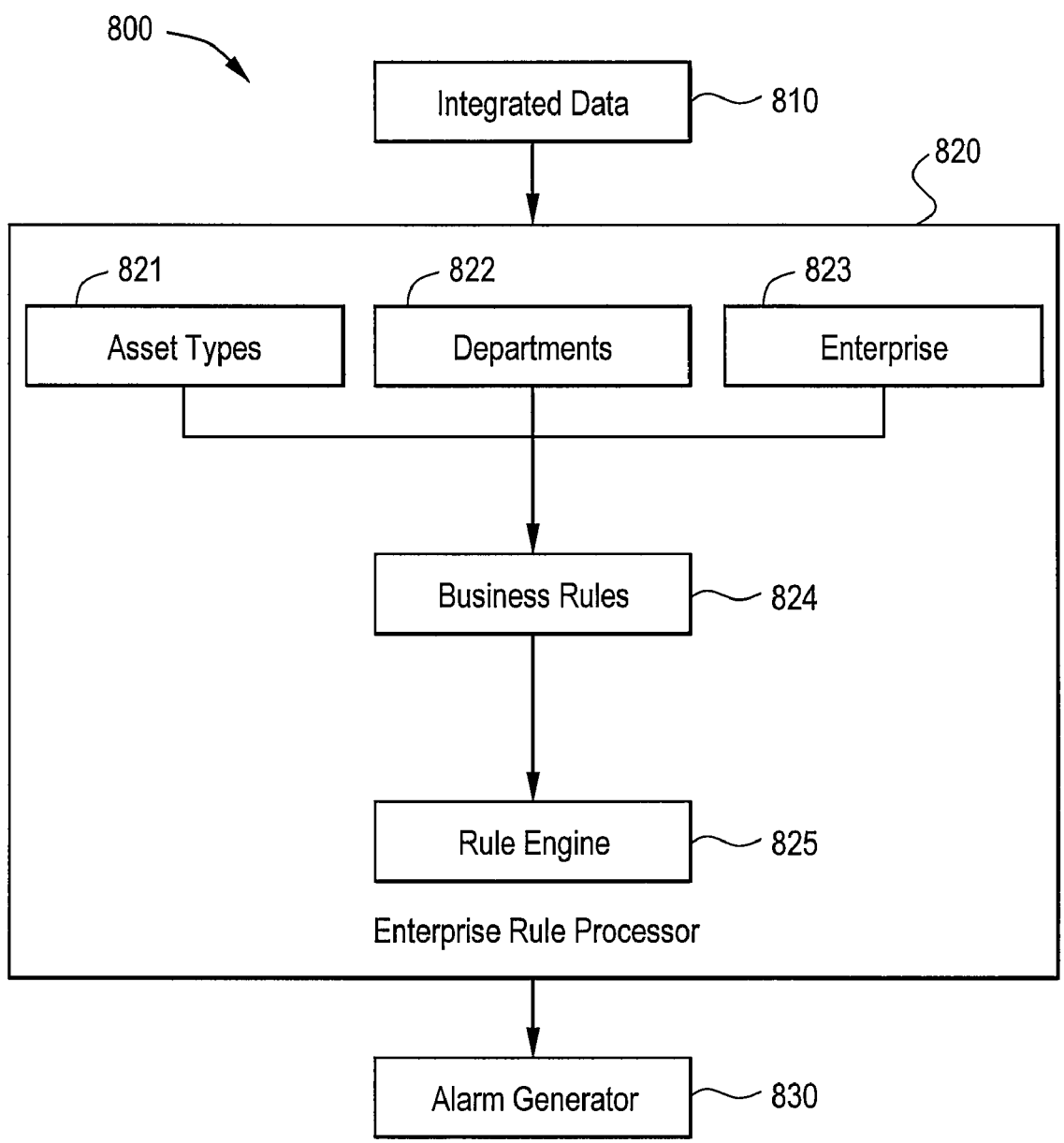
FIG. 8 illustrates a rule processor unit for providing healthcare asset intelligence in accordance with an embodiment of the present invention.

FIG. 8 illustrates a rule processor unit 800 for providing healthcare asset intelligence in accordance with an embodiment of the present invention. The rule processor unit may be similar to the rule engine described above in reference to the service component layer of FIGS. 2 and 3. The rule processor unit 800 includes an integrated data source 810, an enterprise rule processor 820, and an alarm generator 830. The enterprise rule processor 820 includes an asset rules source 821, a department rules source 822, an enterprise rules source 823, an integrated business rules source 824, and a rule engine 825.

The integrated data source 810 is in communication with the enterprise rule processor 820. The enterprise rule processor 820 is in communication with the alarm generator 830. The asset rules source 821, the department rules source 822, and the enterprise rules source 823 are in communication with the integrated business rules source 824. The integrated business rules source 824 is in communication with the rule engine 825.

The integrated data source 810 may be similar to the data warehouse 438, the preprocessors 235 and 335, the preprocessor units 536 and 636, and/or the data integration layer 760. The integrated business rules source 824 may be similar to the rule formatter components of the service component layers 220 and 320. The rule engine 825 may be similar to the rule engine components of the service component layers 220 and 320. The alarm generator 830 may be similar to the visualization layer 710 and the visualization components of the service component layers 220 and 320.

In operation, the integrated data source 810 provides integrated healthcare asset intelligence data to the enterprise rule processor 820, which applies rules to the data. Within the enterprise rule processor 820, the integrated business rules source 824 integrates rules supplied by each of the asset rules source 821, the department rules source 822, and the enterprise rules source and provides the integrated rules to the rule engine 825. The rule engine 825 of the enterprise rule processor 820 applies one or more of the rules provided by the integrated business rules source 824 to some or all of the healthcare asset intelligence data provided by the integrated data source 810. The enterprise rule processor 820 provides to the alarm generator 830 results of the application of these rules to the healthcare asset intelligence data by the rule engine 825. Depending on the results, the alarm generator 830 may generate an alarm. For example, the department rules source 822 may include a neonatal department's rule that at least five nurses be on-site at all times. If the integrated data source 810 provides healthcare asset intelligence data to the enterprise rule processor 820 indicating only four nurses are on-site in the neonatal department, then the alarm generator 830 may generate an alarm once the neonatal department rule is applied to the integrated healthcare asset intelligence data by the rule engine 825.

The asset rules source 821 may provide the integrated business rules source 824 with rules regarding, for example, different asset types such as personnel, devices, or patients.

The department rules source 822 provides the integrated business rules source 824 with rules regarding, for example, the policies of particular departments within a hospital.

The enterprise rules source 823 provides the integrated business rules source 824 with rules regarding, for example, enterprise-wide policies or procedures.

In certain embodiments, the alarm generated by the alarm generator 830 may be presented in numerous ways, including as a visual display, an audible sound, or a paging of a hospital staff member, for example. In certain embodiments, the alarm generator 830 may output an alarm that may be detected by a service component or a service application. For example, an operating room scheduler service application may receive the alarm generated when more than one operations are scheduled for the same operating room. The operating room scheduler service application may be similar to the operating room scheduler described above in reference to the service application layer 210 of FIG. 2.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 9:
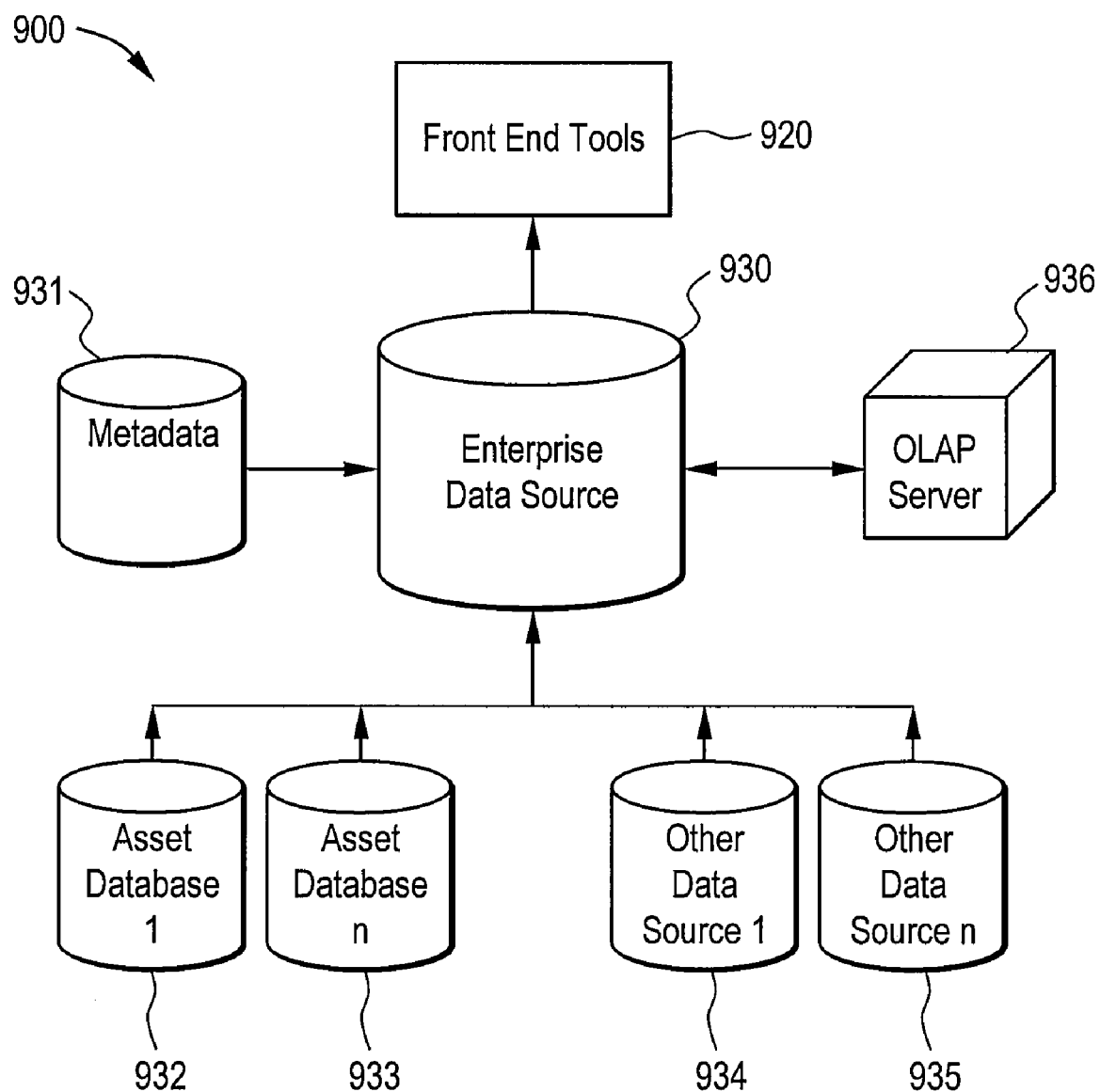
FIG. 9 illustrates a data storage environment for providing healthcare asset intelligence in accordance with an embodiment of the present invention.

FIG. 9 illustrates a data storage environment 900 for providing healthcare asset intelligence in accordance with an embodiment of the present invention. The data storage environment 900 includes an enterprise data source 930, a metadata source 931, a first asset database 932, a second asset database 933, a first other data source 934, a second other data source 935, an online analytical processing (OLAP) server 936, and one or more front end tools 920.

The enterprise data source 930 is in communication with the front end tools 920, the metadata source 931, the first asset database 932, the second asset database 933, the first other data source 934, the second other data source 935, and the OLAP server 936.

The data storage environment 900 may be similar to the data storage environment 400. The enterprise data source 930 may be similar to the data warehouse 438 and the data warehouses of the data layers 230 and 330. The front end tools 920 may be similar to the analysis layer 770 and the service component layers 120, 220, and 320. Each of the first asset database 932 and the second asset database 933 may be similar to the asset databases of the data layers 230 and 330, a data source within the first set of data sources 431, a data source within the second set of data sources 433, the asset maintenance data source 531, the asset configuration data source 532, the asset location data source 534, and the asset utilization data source 535. Each of the first other data source 934 and the second other data source 935 may be similar to the other data sources of the data layers 230 and 330, the flat files source 435, the transactional data source 436, and a data archival within the set of data archivals 437.

In operation, the enterprise data source 930 stores healthcare asset intelligence data from one or more of the metadata source 931, the first asset database 932, the second asset database 933, the first other data source 934, and the second other data source 935. The enterprise data source 930 integrates the healthcare asset intelligence data stored within the other components of the data storage environment 900 for use at an enterprise level by the front end tools 920. The OLAP server 936 is adapted to read integrated healthcare asset intelligence data from and/or write data to the enterprise data source 930 and perform online analysis. The interaction between the OLAP server 936 and the enterprise data source 930 allows for complex or multidimensional data queries to be executed quickly.

The metadata source 931 includes metadata about individual healthcare asset intelligence data items or collections of such items. For example, the metadata source 931 may include the name of a file and its type.

The front end tools may include, for example, one or more service components of the service component layers 220 and 320.

In certain embodiments, the first asset database 932 and the second asset database 933 may be located remotely from one another. Alternatively, the first other data source 934 and the second other data source 935 may be located remotely from one another. In certain embodiments, the number of asset databases and/or the number of other data sources within the data storage environment 900 may be larger or smaller than two.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 10:
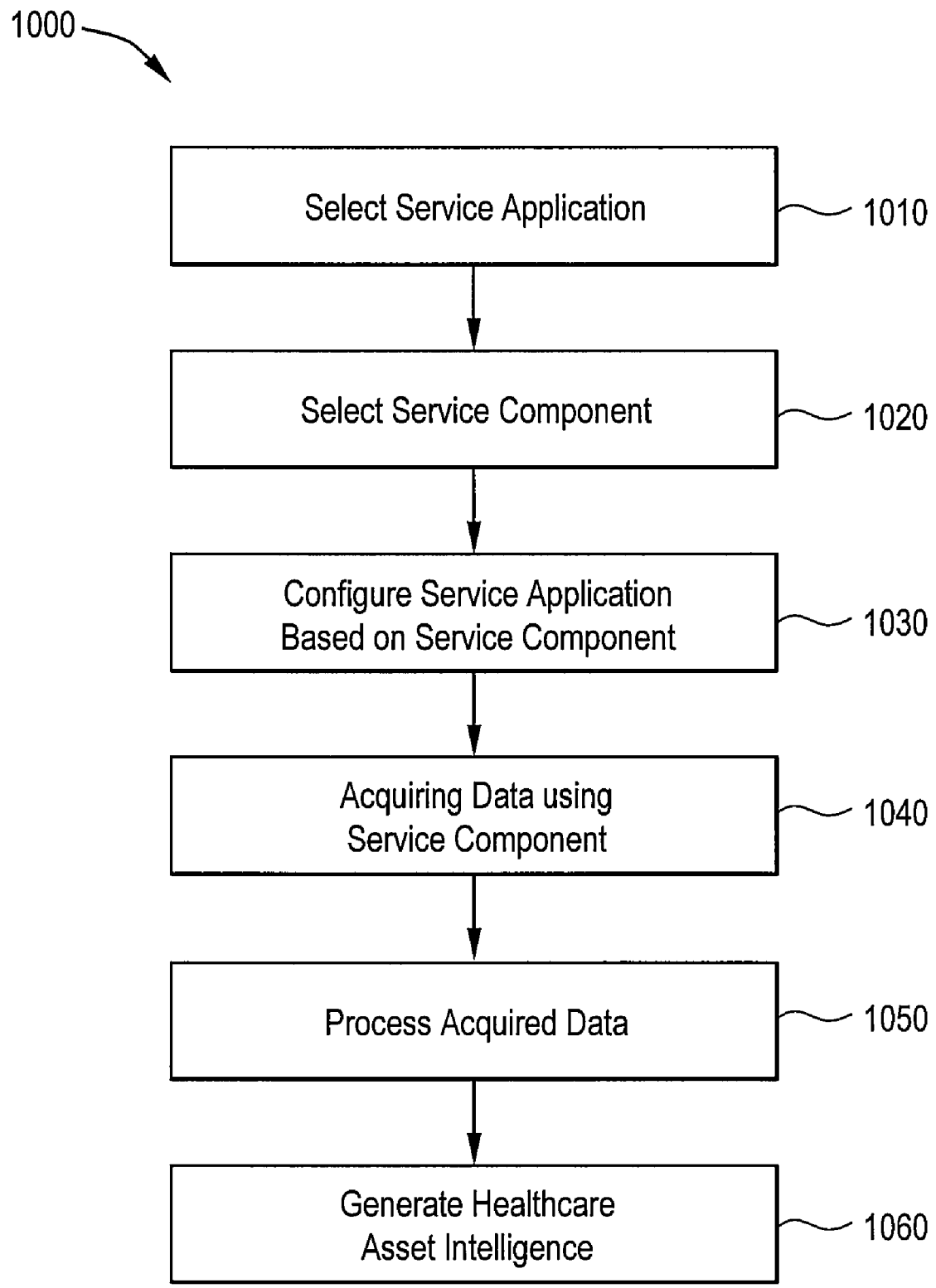
FIG. 10 illustrates a flow diagram for a method for providing healthcare asset intelligence in accordance with an embodiment of the present invention.

FIG. 10 illustrates a flow diagram for a method 1000 for providing healthcare asset intelligence in accordance with an embodiment of the present invention. The method 1000 includes the following steps, which will be described below in more detail. At step 1010, a service application is selected. At step 1020, one or more service components are selected. At step 1030, the service application is configured based at least in part on the one or more service applications selected. At step 1040, the one or more service components acquire healthcare asset intelligence data. At step 1050, the acquired healthcare asset intelligence data is processed. At step 1060, the healthcare asset intelligence is generated based at least in part on the processing of the acquired healthcare asset intelligence data.

At step 1010, the service application is selected. For example, an asset optimizer application may be selected in order to optimize the use of a particular asset. The asset optimizer application may be similar to the asset optimizer applications within the service application layers 210 and 310. In certain embodiments, a service application may be selected by a user of a healthcare asset intelligence system using, for example, a user interface that may be similar to the user interfaces 545 and 645. The healthcare asset intelligence system may be similar to the systems 100, 200, 300, 500, and 600.

At step 1020, the one or more service components are selected. For example, if the asset optimizer application is selected at step 1010, then as described above with regard to the example illustrated in FIG. 3, five service components may be used in combination in order to execute the asset optimizer application: a filtering component, a visualization component, an optimizer component, location service component, and a rule engine component. In certain embodiments, the service components needed to run each service application are pre-determined so that when a service application is selected, the appropriate service components are automatically selected for use. In certain embodiments, the user may customize an existing service application or construct a new service application by adding or subtracting service components for use by the service application. In certain embodiments, the service components may be integrated using a service integrator, such as one of the service integrators 225 or 325 described above.

Characteristics of each service component may be available in the service component layer. In certain embodiments, the user may select one or more of the service components from a plurality of service components displayed on the user interface, for example. One or more characteristics may be associated with each service component and displayed on the user interface. A characteristic may describe a service component's operation and/or requirements. For example, the healthcare asset intelligence data the service component receives and the healthcare asset intelligence the service component generates may comprise the service component's characteristics.

In certain embodiments, the service application may automatically select the one or more service components based at least in part on each component's characteristics. For example, if the asset optimizer application is selected, the filtering component, the visualization component, the optimizer component, the location service component, and the rule engine component may be selected automatically based at least in part on each component's characteristics.

The plurality of service components may be in a service-oriented architecture. Each service component may be adapted to acquire healthcare asset intelligence data from a data warehouse, such as the data warehouse 438, for example.

At step 1030, the service application is configured based at least in part on the one or more service components selected. The service application may be adapted to generate the healthcare asset intelligence using the selected service component. For example, as described above, the service application may be configured to communicate with and/or query the five service components. The five service components used to execute the asset optimizer application may be prepared and/or integrated once the asset optimizer application is selected.

In situations where the service application calls for the use of multiple service components, each service component may perform its function in a specific order to ensure the integrity of healthcare asset intelligence data that is acquired by the service components. In certain embodiments, this regulation of access to healthcare asset intelligence data by multiple service components is provided using service-oriented computing (SOC). In certain embodiments, the service application may be configured to retrieve the healthcare asset intelligence from the one or more service components consecutively and/or concurrently, for example. For example, the user may configure the service application or the service application may be configured automatically by the selection of the one or more service components.

In certain embodiments, the method 1000 may be performed with only steps 1020 and 1030. In certain embodiments, the method 1000 may be performed without step 1030. In certain embodiments, the step 1020 may further include the step 1030. In certain embodiments, the method 1000 may be preformed with only steps 1040, 1050, and 1060.

At step 1040, the one or more service components acquire healthcare asset intelligence data. In certain components, each service component may retrieve healthcare asset intelligence data from a data warehouse. The data warehouse may be similar to the data warehouse 438 or the enterprise data source 930. For example, if the asset optimizer application is selected at step 1010, the location service component may acquire healthcare asset intelligence data relating to the locations of a hospital's IV pumps within the hospital.

As described above, the order in which the one or more service components acquire healthcare asset intelligence data may be regulated in order to maintain the data's integrity. Each service component may retrieve healthcare asset intelligence data from a data layer, which may be similar to the data layers 130, 230, and 330. The service components may be part of a service component layer, such as the service component layers 120, 220, and 320 described above, for example. The data layer may include one or more preprocessors, such as the preprocessors 235 and 335 and the preprocessor units 536 and 636, as described above. The preprocessors and/or the service integrators may limit the one or more service components to access the healthcare asset intelligence data serially, as described above.

The data warehouse and the one or more service components may be stored at a centralized site, such as the centralized site 560 and 660 and the centralized site discussed above in reference to FIGS. 2 and 4.

At step 1050, the acquired healthcare asset intelligence data is processed. For example, the healthcare asset intelligence data acquired by the location service component and the optimizer component may be compared or analyzed according to an established priority of assets in order to provide healthcare asset intelligence relevant to optimizing the assets of a healthcare enterprise. In certain embodiments, the processing of step 1050 is performed at the service application level. In certain embodiments, some or all of the processing of step 1050 is performed by the one or more service components. A service-oriented architecture (SOA) of the healthcare asset intelligence system is used to process the healthcare asset intelligence data. The SOA may be similar to the SOA described above in reference to FIGS. 1, 2, and 3.

At step 1060, healthcare asset intelligence is generated based at least in part on the processing of the acquired healthcare asset intelligence data. The healthcare asset intelligence may be generated using the SOC of the healthcare asset intelligence system. The SOC may be similar to the SOC described above in reference to FIGS. 1, 2, and 3. For example, assuming the asset optimizer application were selected at step 1010, the healthcare asset intelligence generated at step 1060 may include a recommendation that certain hospital staff members be reassigned from one department to another for a given time due to an above-normal demand for additional staff in a particular department. In certain embodiments, some or all of the healthcare asset intelligence may be generated automatically based at least in part on the service application and/or service components selected. In certain embodiments, a user may request a specific type of healthcare asset intelligence, such as a recommendation that will provide asset management decision support, in addition to any healthcare asset intelligence that is automatically generated.

The embodiments, configurations, and functionalities described above with reference to FIGS. 1-9 may also apply to the steps of the method 1000 for providing healthcare asset intelligence.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method 1000 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 11:
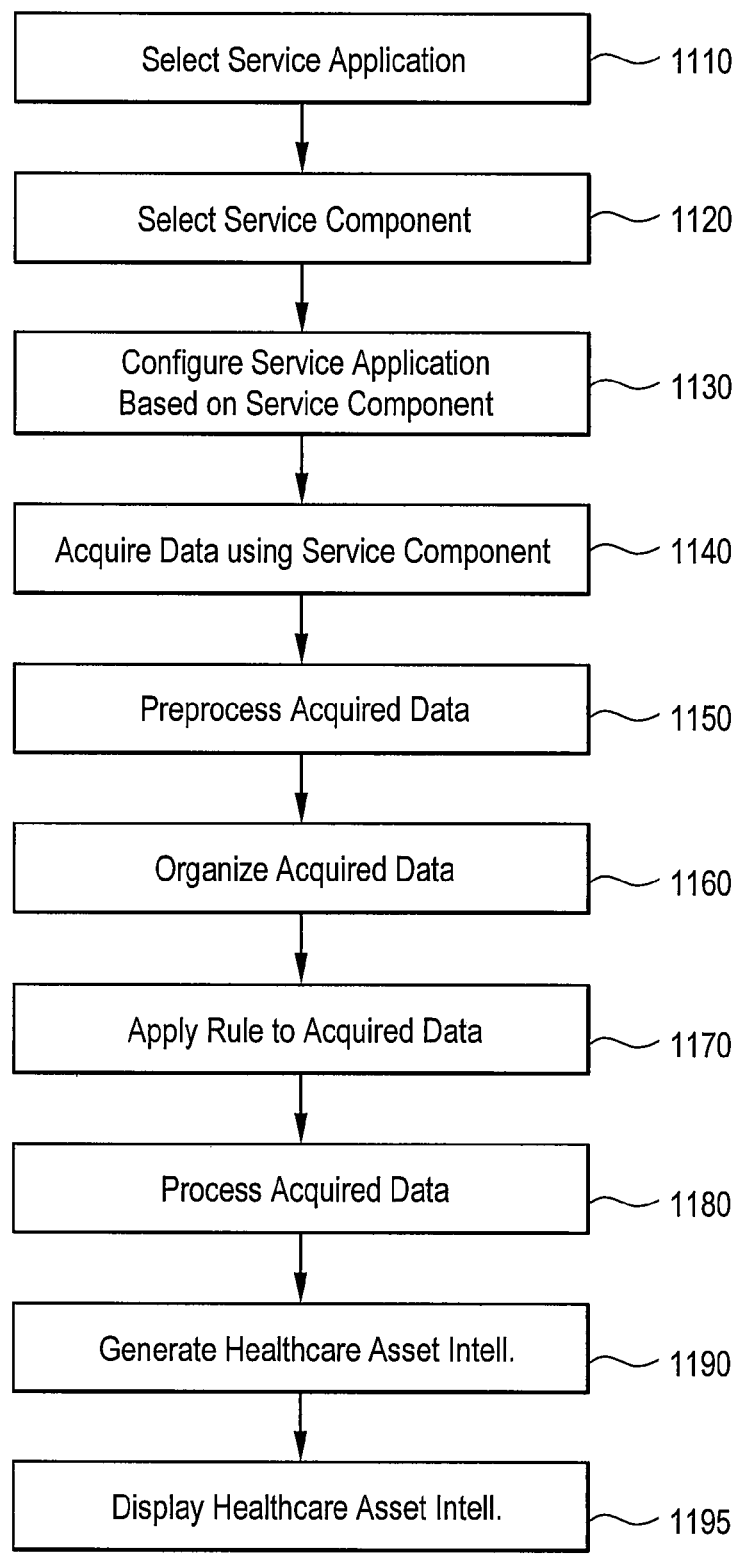
FIG. 11 illustrates a flow diagram for a method for providing healthcare asset intelligence in accordance with an embodiment of the present invention.

FIG. 11 illustrates a flow diagram for a method 1100 for providing healthcare asset intelligence in accordance with an embodiment of the present invention. The method 1100 includes the following steps, which will be described below in more detail. At step 1110, a service application is selected. At step 1120, one or more service components are selected. At step 1130, the service application is configured based at least in part on the one or more service components selected. At step 1140, the service components acquire healthcare asset intelligence data. At step 1150, the healthcare asset intelligence data is preprocessed. At step 1160, the healthcare asset intelligence data is organized. At step 1170, one or more rules are applied to the healthcare asset intelligence data. At step 1180, the healthcare asset intelligence data is processed. At step 1190, the healthcare asset intelligence is generated based at least in part on the processing of the healthcare asset intelligence data. At step 1195, the healthcare asset intelligence is displayed.

The method 1100 may be similar to the method 1000.

At step 1110, the service application is selected. For example, an asset optimizer application may be selected in order to optimize the use of a particular asset. The step 1110 may be similar to the step 1010.

At step 1120, the one or more service components are selected. For example, if the asset optimizer application is selected at step 1110, then a filtering component, a visualization component, an optimizer component, location service component, and a rule engine component may be selected to be integrated together in order to execute the asset optimizer application. The step 1120 may be similar to the step 1020.

At step 1130, the service application is configured based at least in part on the one or more service components. For example, as described above, the service application may be configured to communicate with and/or query the five service components. The five service components used to execute the asset optimizer application may be prepared and/or integrated once the asset optimizer application is selected. The step 1130 may be similar to the step 1030.

At step 1140, the service components acquire the healthcare asset intelligence data. For example, the location service component may acquire healthcare asset intelligence data relating to the locations of a hospital's IV pumps within the hospital. The step 1140 may be similar to the step 1040.

At step 1150, the healthcare asset intelligence data is preprocessed. In certain embodiments, the preprocessing of step 1150 may take place automatically prior to or upon acquisition of the healthcare asset intelligence data. In certain embodiments, the preprocessing of step 1150 may be selectively employed by a user.

A preprocessor unit may perform the step 1150. The preprocessor unit may be similar to the preprocessor units 235, 335, 536, and 636 described above. The preprocessing may include formatting, integrating, and/or encrypting the healthcare asset intelligence data as described above. For example, if the acquired healthcare asset intelligence data includes data of varying formats or security levels, some or all of the acquired healthcare asset intelligence data may be reformatted and/or encrypted in order to facilitate later processing of the data.

At step 1160, the healthcare asset intelligence data is organized. In certain embodiments, one or more cluster factors may be employed to organize some or all of the acquired healthcare asset intelligence data. In certain embodiments, organization according to cluster factors may occur automatically. The data may be organized and/or aggregated in a data warehouse, a centralized site, and/or a back office. The data warehouse may be similar to the data warehouse described above in reference to FIG. 1, the data warehouse 438, and the enterprise data source 930. The centralized site may be similar to the centralized sites 560 and 660 described above. The back office may be similar to the back office 570 described above.

For example, the acquired healthcare asset intelligence data may be organized according to a clustering factor that calls for the grouping of data for hospitals of a certain size and type.

At step 1170, the one or more rules are applied to the healthcare asset intelligence data. In certain embodiments, the application of rules at step 1170 is accomplished by a service component that is associated with the service application selected at step 1110. For example the service component associated with the service application may be the rule engine component, which may be similar to the rule engine component described above in reference to FIGS. 1, 2, 3, and 10, and the rule engine 825.

For example, a particular department of a hospital, such as a neonatal department, may have a rule that the department must have at least five nurses on-site at all times. If the neonatal department's rule is applied at step 1170 and the healthcare asset intelligence data indicates that only four nurses are currently on-site in the neonatal department, then an alarm or other signal may be generated as described above in reference to FIG. 8 or a report may also be prepared.

At step 1180, the healthcare asset intelligence data is processed. For example, the healthcare asset intelligence data acquired by the rule engine component and the optimizer component may be compared and/or analyzed according to an established priority of assets in order to provide healthcare asset intelligence relevant to optimizing the assets of a healthcare environment. The step 1180 may be similar to the step 1050.

At step 1190, the healthcare asset intelligence is generated based at least in part on the processing of the acquired healthcare asset intelligence data. For example, if the asset optimizer application was selected at step 1110, the healthcare asset intelligence generated at step 1190 may include a recommendation that certain hospital staff members be reassigned from one department to another for a period of time due to an above-normal demand for additional staff in a particular department. The step 1190 may be similar to the step 1060.

The asset optimizer application may help utilize assets optimally, which may include replacing assets, using assets more or less frequently, servicing assets more or less frequently, and/or purchasing cheaper or more expensive assets, for example. The asset optimizer application may help improve the productivity of hospital staff and patient care.

At step 1195, the healthcare asset intelligence is displayed. In certain embodiments, the visual display provided at step 1195 is accomplished by a service component that is associated with the service application selected at step 1110. This service component may be similar to the visualization layer 710 and the visualization component of the service component layers 220 and 320. In certain embodiments, the healthcare asset intelligence may be communicated to a user in a variety of ways, including through an audible sound, a page, or some other type of notification. For example, if a staff reassignment recommendation is generated at step 1190, that recommendation may be displayed visually on the computer screen of the hospital's staff manager. As another example, the healthcare asset intelligence data may be displayed on a nursing dashboard, which may display information concerning certain healthcare assets, such as the location of patients, equipment, physicians, and/or nurses on a hospital floor.

The certain embodiments, configurations, and functionalities described above with regard to FIGS. 1-10 also apply to the steps of the method 1100 for providing healthcare asset intelligence.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method 1100 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 12:
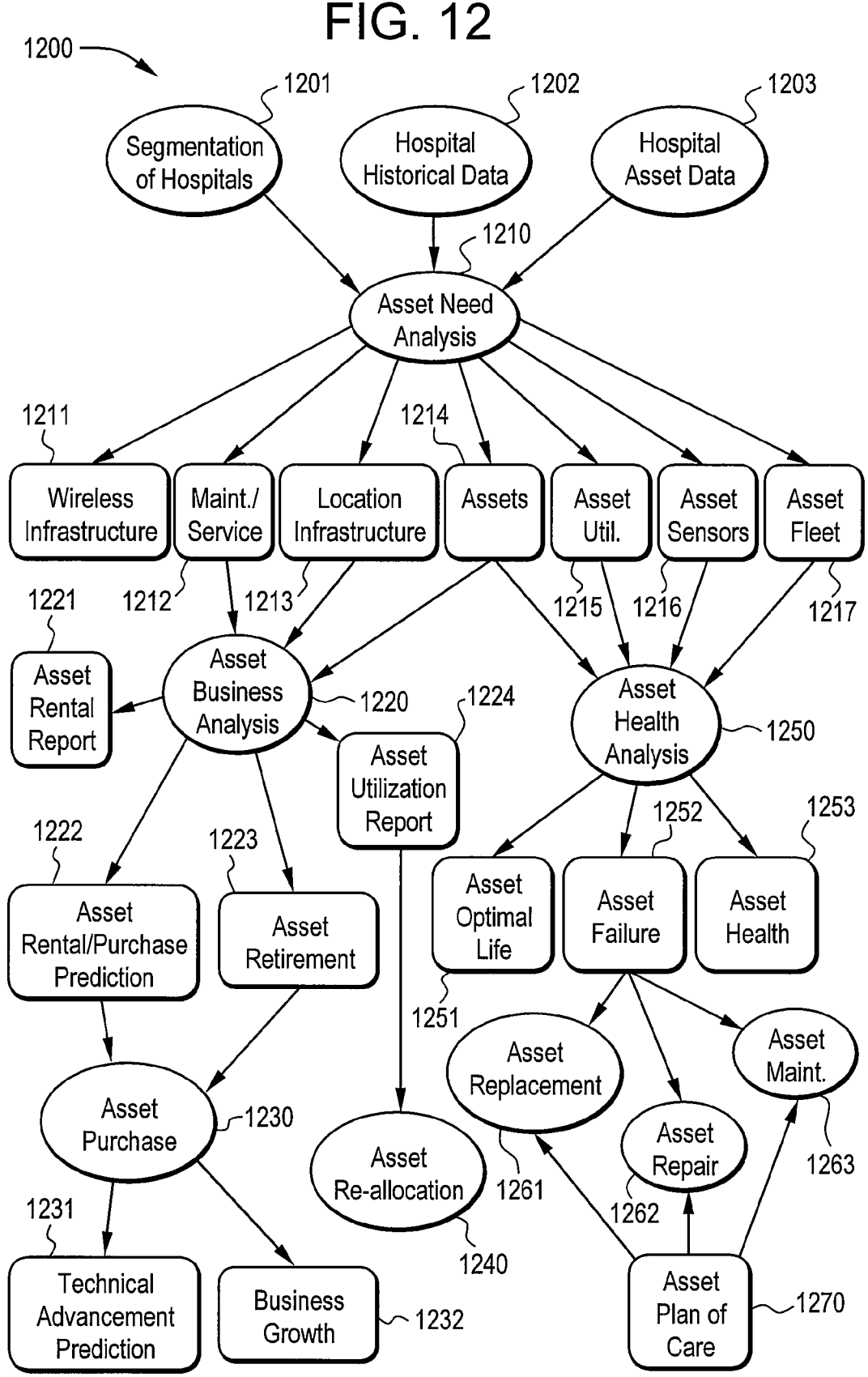
FIG. 12 illustrates a system for providing healthcare asset intelligence in accordance with an embodiment of the present invention.

FIG. 12 illustrates a system 1200 for providing healthcare asset intelligence in accordance with an embodiment of the present invention. In certain embodiments, the system 1200 is adapted for use within a hospital enterprise. In certain embodiments, the system 1200 is adapted for use within an enterprise which includes healthcare providers other than hospitals, such as an enterprise including an assisted living facility, for example. The system 1200 includes a hospital segmentation data source 1201, a hospital historical data source 1202, a hospital asset data source 1203, an asset need analysis component 1210, a wireless infrastructure 1211, a maintenance component 1212, a location infrastructure 1213, one or more assets 1214, an asset utilization component 1215, one or more asset sensors 1216, an asset fleet analysis component 1217, an asset business analysis component 1220, an asset rental report component 1221, an asset rental/purchase prediction component 1222, an asset retirement component 1223, an asset utilization report component 1224, an asset purchase component 1230, a technical advancement prediction component 1231, a business growth component 1232, an asset reallocation component 1240, an asset health analysis component 1250, an asset life optimizer 1251, an asset failure component 1252, an asset health analysis component 1253, an asset replacement component 1261, an asset repair component 1262, an asset maintenance component 1263, and an asset plan of care component 1270.

The asset need analysis component 1210 is in communication with the hospital segmentation data source 1201, the hospital historical data source 1202, the hospital asset data source 1203, the wireless infrastructure 1211, the maintenance component 1212, the location infrastructure 1213, the one or more assets 1214, the asset utilization component 1215, the one or more asset sensors 1216, and the asset fleet analysis component 1217. The asset business analysis component 1220 is in communication with the maintenance component 1212, the location infrastructure 1213, the one or more assets 1214, the asset rental report component 1221, the asset rental/purchase prediction component 1222, the asset retirement component 1223, and the asset utilization report component 1224. The asset purchase component 1230 is in communication with the asset rental/purchase prediction component 1222, the asset retirement component 1223, the technical advancement prediction component 1231, and the business growth component 1232. The asset utilization report component 1224 is in communication with the asset reallocation component 1240. The asset health analysis component 1250 is in communication with the one or more assets 1214, the asset utilization component 1215, the one or more asset sensors 1216, the asset fleet analysis component 1217, the asset life optimizer 1251, the asset failure component 1252, and the asset health analysis component 1253. The asset failure component 1252 is in communication with the asset replacement component 1261, the asset repair component 1262, and the asset maintenance component 1263. The asset plan of care component 1270 is in communication with the asset replacement component 1261, the asset repair component 1262, and the asset maintenance component 1263.

The components of the system 1200 may be similar to certain components of the FIGS. 1-11 described above.

In operation, the system 1200 provides healthcare asset intelligence for efficiently managing the enterprise's assets. The hospital segmentation data source 1201 provides healthcare asset intelligence data to the asset need analysis component 1210 relating to the segmentation or clustering of different hospitals within the enterprise, such as the number of hospitals with cardiovascular surgery departments, for example. The hospital historical data source 1202 provides healthcare asset intelligence data to the asset need analysis component 1210, such as data relating to the historical usage of and need for healthcare assets during a particular period of time. The hospital asset data source 1203 provides healthcare asset intelligence data to the asset need analysis component 1210 relating to, for example, the number of hospital beds within a particular hospital. The hospital asset data source 1203 may be similar to the data warehouse described above in reference to FIG. 1, the data warehouse 438, the enterprise data source 930, and any other data source described above in reference to FIGS. 1-11.

The asset need analysis component 1210 uses this healthcare asset intelligence data to provide healthcare asset intelligence data regarding any demand or need for healthcare assets in the enterprise, such as, for example, the asset needs of a particular hospital within the enterprise, to each of the wireless infrastructure 1211, the maintenance component 1212, the location infrastructure 1213, the one or more assets 1214, the asset utilization component 1215, the one or more asset sensors 1216, and the asset fleet analysis component 1217. The maintenance component 1212 provides healthcare asset intelligence data to the asset business analysis component 1220 relating to the maintenance or service schedule for a particular hospital's machines and equipment, such as the maintenance schedule for a hospital's respirator machines, for example. The location infrastructure 1213 provides healthcare asset intelligence data to the asset business analysis component 1220 relating to the location of a hospital's assets. One or more of the assets 1214 provide healthcare asset intelligence data to the asset business analysis component 1220 that may include information related to the number of assets in a hospital or enterprise, such as the number of cardiac defibrillators housed within a hospital, for example.

The asset business analysis component 1220 provides healthcare asset intelligence data, such as information about asset surpluses and efficiency, to each of the asset rental report component 1221, the asset rental/purchase prediction component 1222, the asset retirement component 1223, and the asset utilization report component 1224. The asset rental report component 1221 may, for example, generate a report summarizing the number of assets a hospital within the enterprise is currently renting from rental companies. The asset rental/purchase prediction component 1222 may, for example, generate a prediction of which assets may need to be rented or purchased by a hospital and when that transaction should take place. The asset rental/purchase prediction component 1222 provides this healthcare asset intelligence data to the asset purchase component 1230. The asset retirement component 1223 provides healthcare asset intelligence data, such as the time at which a particular hospital asset should be retired, to the asset purchase component 1230 and other asset management components.

Based at least in part on the healthcare asset intelligence data provided by the asset rental/purchase prediction component 1222 and the asset retirement component 1223, the asset purchase component 1230 may automatically, or through interaction with a user of the system 1200, arrange for assets to be purchased for the hospital. In certain embodiments, the asset purchase component 1230 may generate a list of healthcare assets to purchase and recommended purchase periods. In certain embodiments, the asset purchase component 1230 may provide recommendations as to whether an asset should be purchased, leased, or rented as a mode of procurement. The asset purchase component 1230 may provide healthcare asset intelligence data relating to the recommended asset purchases to each of the technical advancement prediction component 1231 and the business growth component 1232. The technical advancement prediction component 1231 may, for example, predict the lifetime of the purchased assets before they would need replacement due to technical advancements in the field. The business growth component 1232 may generate healthcare asset intelligence data relating to tracking and predicting business growth for the enterprise or hospital, such as data relating to practice areas that may be new to the hospital based at least in part on the assets being purchased or recommended for purchase by the asset purchase component 1230.

In addition, the asset utilization report component 1224 provides healthcare asset intelligence data to the asset reallocation component 1240 relating to the extent to which one or more asset types are currently being utilized by the hospital. Based at least in part on this data, the asset reallocation component 1240 may automatically, or through interaction with the user of the system 1200, reallocate assets within the hospital or between multiple hospitals within the enterprise.

In operation, the system 1200 also provides analytical tools for evaluating the health of a hospital's assets. The one or more assets 1214 provide healthcare asset intelligence data to the asset health analysis component 1250 based at least in part on the number and/or location of healthcare assets in the hospital or enterprise, such as, for example, the number of cardiac defibrillators housed within the hospital. The asset utilization component 1215 provides healthcare asset intelligence data to the asset health analysis component 1250 relating to the use of the healthcare assets in the hospital or enterprise, such as, for example, the number of respirator machines currently being used within the hospital. The one or more asset sensors 1216 provide healthcare asset intelligence data to the asset health analysis component 1250 relating to the status and/or location of the healthcare assets in the enterprise, such as, for example, the temperature of a particular asset. The asset fleet analysis component 1217 provides healthcare asset intelligence data to the asset health analysis component 1250 including the healthcare asset intelligence data of other hospitals within the enterprise that may be used for comparison purposes in analyzing the health of the particular hospital's assets. By utilizing healthcare asset intelligence data from the assets 1214, the asset utilization component 1215, the asset sensors 1216, and the asset fleet analysis component 1217, the asset health analysis component 1250 is able to analyze the health of an asset more accurately than by simply referring to, for example, a manufacturer's suggested lifespan and maintenance schedule. For example, an IV pump that is actually in use only 10 percent of the time may require less frequent routine maintenance in comparison to IV pumps being utilized 80 percent of the time.

When certain healthcare asset intelligence data is combined at a central location, a fleet-level analysis may be carried out. For example, clusters may be developed based on asset utilization and used to decide the failures of assets belonging to a cluster when asset utilization data is not available to determine usage-based maintenance. The fleet-level analysis may allow hospitals without past utilization data to use fleet-level data to make healthcare management determinations.

The asset health analysis component 1250 provides healthcare asset intelligence data, such as information about the health of a particular asset or of similar known assets to each of the asset life optimizer 1251, the asset failure component 1252, and the asset health analysis component 1253. The asset life optimizer 1251 may generate, for example, a prediction of the remaining lifespan of the particular asset. The asset health analysis component 1253 may provide, for example, an analysis of the asset's health in relation to comparable assets within the enterprise. If the asset is currently failing, for example, the asset failure component 1252 may provide healthcare asset intelligence data regarding the asset's failure to an appropriate component in order to remedy the failure. If the asset has completely failed and is not repairable, then the asset failure component 1252 may notify the asset replacement component 1261 that the asset should be replaced. If the asset merely needs routine maintenance in order to correct the failure, then the asset failure component 1252 may notify the asset maintenance component 1263 that the asset should undergo routine maintenance. If the asset cannot be corrected through routine maintenance but can be repaired, then the asset failure component 1252 may notify the asset repair component 1262 that the asset should be repaired. Each of the asset replacement component 1261, the asset repair component 1262, and the asset maintenance component 1263 also receive healthcare asset intelligence data from the asset plan of care component 1270 that may include, for example, the typical (usage-based) plan of care for an asset of the type being analyzed.

In certain embodiments, an asset may be replaced when the asset is not utilized optimally due to excessive breakdowns which require more repair and maintenance than is optimal.

The system 1200 comprises an embodiment of the present invention wherein the each of the components of the system described above may be either a data source from a data layer, a service component from a service component layer, and a service application from a service application layer. The data layer, the service component layer, and the service application layer may be similar to the data layer 130, 230, and 330, the service component layer 120, 220, and 320, and the service application layer 110, 210, and 310, respectively, as described above.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

Figure 13:
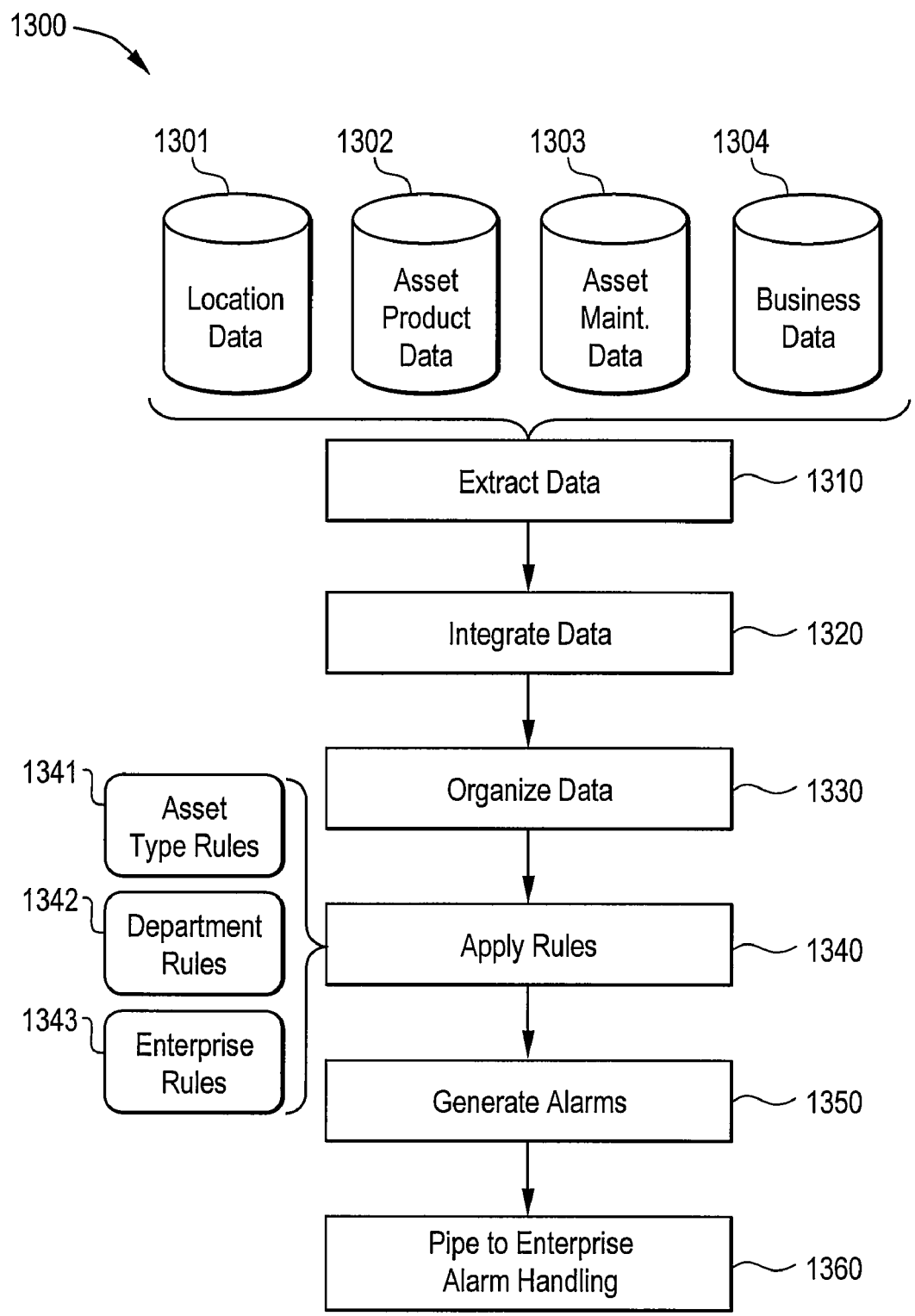
FIG. 13 illustrates a flow diagram for a method for providing healthcare asset intelligence in accordance with an embodiment of the present invention.

FIG. 13 illustrates a flow diagram for a method 1300 for providing healthcare asset intelligence in accordance with an embodiment of the present invention. The method 1300 includes the following steps, which will be described below in more detail. At step 1310, healthcare asset intelligence data is extracted from a location data source 1301, an asset product data source 1302, an asset maintenance data source 1303, and/or a business data source 1304. At step 1320, the extracted healthcare asset intelligence data is integrated. At step 1330, the integrated healthcare asset intelligence data is organized. At step 1340, one or more rules are applied to the organized healthcare asset intelligence data. The one or more rules applied at step 1340 include rules provided by an asset rules source 1341, a department rules source 1342, and/or an enterprise rules source 1343, or the rules can be generated by the data itself in certain embodiments. For example, historical usage data may be used to generate minimum and maximum asset limits before an order for replenishment can be placed. At step 1350, an alarm is generated based at least in part on the application of the one or more rules to the organized healthcare asset intelligence data. At step 1360, the alarm is sent to an enterprise alarm handling unit.

The location data source 1301 may be similar to the asset location data source 534 and the patient/personnel location data source 634. The asset product data source 1302 may be similar to the asset configuration data source 532. The asset maintenance data source 1303 may be similar to the asset maintenance data source 531. The business data source 1304 may be similar to the business data sources 537 and 637. The asset rules source 1341 may be similar to the asset rules source 821. The department rules source 1342 may be similar to the department rules source 822. The enterprise rules source 1343 may be similar to the enterprise rules source 823.

The step 1310 may be similar to the step 1040 and the step 1140. The step 1320 may be similar to the step 1150. The step 1330 may be similar to the step 1160. The step 1340 may be similar to the step 1170.

At step 1310, the healthcare asset intelligence data is extracted. The healthcare asset intelligence data may be extracted from the location data source 1301, the asset product data source 1302, the asset maintenance data source 1303, and/or the business data source 1304. In certain embodiments, each of these data sources may include different types of healthcare asset intelligence data. The extraction of data from these sources may take place automatically. In certain embodiments, a user may choose to extract data from one or more of the location data source 1301, the asset product data source 1302, the asset maintenance data source 1303, and the business data source 1304. In certain embodiments, a data warehouse may extract the healthcare asset intelligence data. The data warehouse may be similar to the data warehouse described above in reference to FIG. 1 and FIG. 12, the data warehouse 438, and the enterprise data source 930.

At step 1320, the extracted healthcare asset intelligence data is integrated. For example, if the healthcare asset intelligence data extracted at step 1310 originates from a variety of data sources, then some or all of the extracted data may be integrated in order to facilitate further processing. The data may be integrated by a preprocessor unit. The preprocessor unit may be similar to the may be similar to the preprocessors 235 and 335, the preprocessor units 536 and 636, and the preprocessor unit described above in reference to FIGS. 10 and 11.

At step 1330, the integrated healthcare asset intelligence data is organized. The data warehouse and/or the preprocessor may organize the integrated healthcare asset intelligence data. For example, the integrated healthcare asset intelligence data may be organized according to a clustering factor that calls for the grouping of data for hospitals of a certain size, asset utilization, and/or DRGs. In this example, healthcare asset intelligence data relating to the assets of hospitals having fewer than 100 patient rooms may all be grouped together.

At step 1340, one or more rules are applied to the organized healthcare asset intelligence data. As described above, the rules applied at step 1340 may include rules provided by the asset rules source 1341, the department rules source 1342, and/or the enterprise rules source 1343. For example, the asset rules source 1341 may provide rules regarding, for example, different asset types such as personnel, devices, and patients. The department rules source 1342 may provide rules regarding, for example, the policies of particular departments within a healthcare environment. The enterprise rules source 1343 may provide, for example, enterprise-wide policies or procedures. In addition to the rules, certain asset management determinations may be made based upon the healthcare asset data, such as reorder determinations based upon asset utilization, for example. The one or more rules from these rules sources are applied to some or all of the organized healthcare asset intelligence data. An enterprise rule processor similar to the enterprise rule processor 820 may perform the step 1340.

At step 1350, an alarm is generated based at least in part on the application of the one or more rules to the organized healthcare asset intelligence data. For example, a hospital may have a rule that five empty hospital beds must be available at all times in order to accommodate spikes in demand to handle emergency cases. If this rule is applied at step 1350 and the healthcare asset intelligence data indicates that only three hospital beds within the hospital are currently empty, then an alarm may be generated. An alarm generator similar to the alarm generator 830 may perform the step 1350.

At step 1360, the alarm is sent to the enterprise alarm handling unit. For example, if an alarm is generated within one branch of a larger enterprise, then that alarm is provided to the enterprise alarm handling unit, which may synthesize all alarms generated within the enterprise. This functionality may be useful, for example, in allowing the enterprise alarm handling unit to observe an alarm indicating a shortage of IV pumps within one branch of the enterprise and then check to see whether other branches within the enterprise have excess IV pumps that may be used to remedy the shortage within the first branch. The alarm generator may send the alarm to the enterprise alarm handling unit.

The certain embodiments, configurations, and functionalities described above with regard to FIGS. 1-12 also may apply to the steps of the method 1300 for providing healthcare asset intelligence.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method 1300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 14:
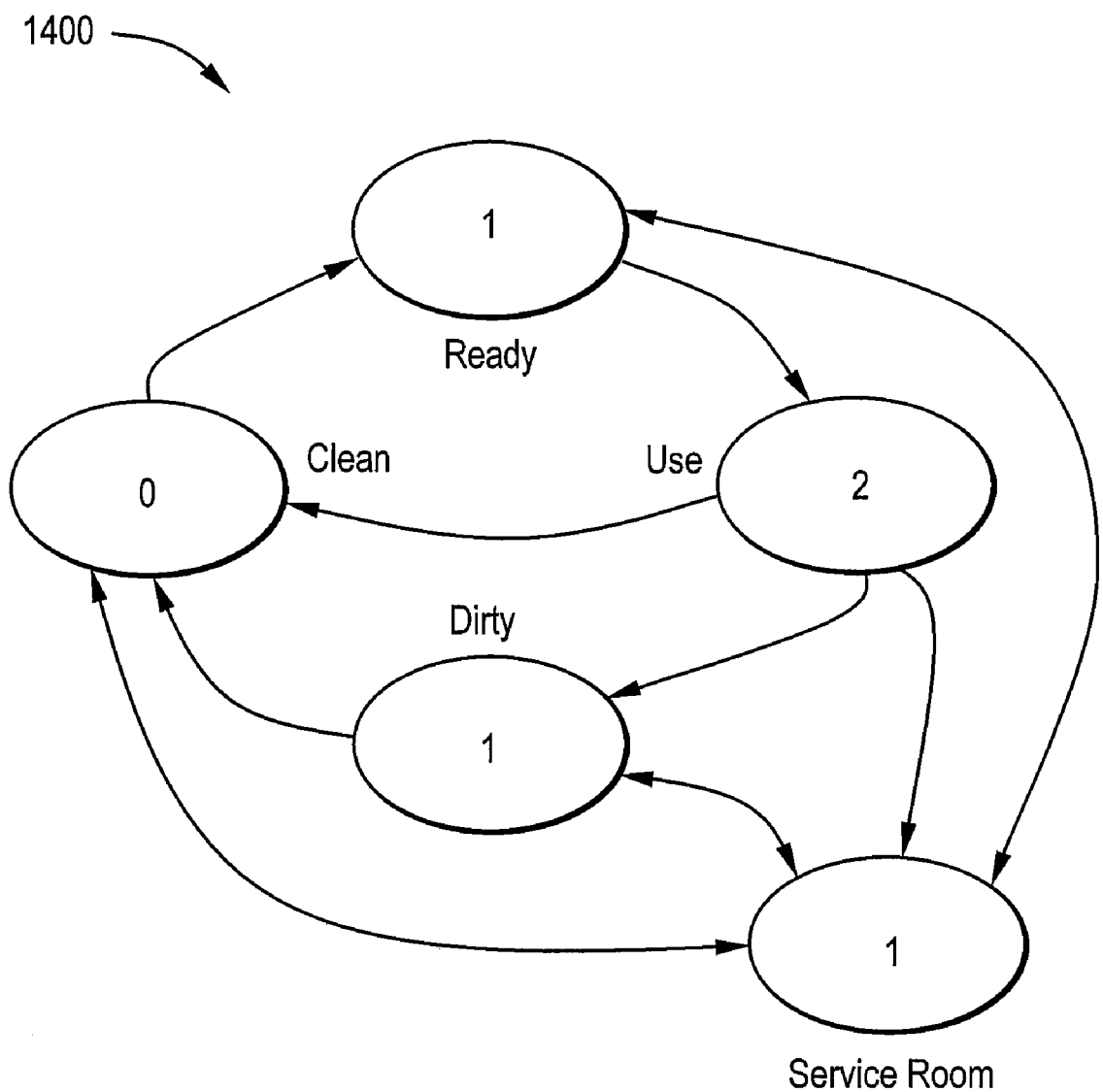
FIG. 14 illustrates an asset state flow diagram for IV pumps in accordance with an embodiment of the present invention.

FIG. 14 illustrates an asset state flow diagram 1400 for IV pumps in accordance with an embodiment of the present invention. The asset flow chart may be stored by a maintenance component, such as the asset maintenance data source 531, the maintenance component 1212, or the asset plan of care component 1270, as described above.

The components, elements, and/or functionality of the interface(s) and system(s) described above may be implemented alone or in combination in various forms of hardware, firmware, and/or as a set of instructions in software, for example. Certain embodiments may be provided as a set of instructions residing on a computer-readable medium, such as a memory or hard disk, for execution on a general purpose computer or other processing device, such as, for example, one or more dedicated processors.

In the present specification, use of the singular includes the plural except where specifically indicated. In the present specification, any of the functions recited herein may be performed by one or more means for performing such functions.

Thus, certain embodiments of the present invention provide a method for providing healthcare asset intelligence using a service-oriented architecture and service-oriented computing. Further, certain embodiments of the present invention provide for a system for providing healthcare asset intelligence using a service-oriented architecture and service-oriented computing. Certain embodiments provide a technical effect of providing healthcare asset intelligence using a service-oriented architecture and service-oriented computing.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, certain embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Certain embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Certain embodiments of the present invention may be practiced in a networked environment using logical connections to one or more remote computers having processors. Logical connections may include a local area network (LAN) and a wide area network (WAN), which are presented here by way of example and not limitation. Such networking environments are commonplace in office-wide or enterprise-wide computer networks, intranets, and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

Although the dependent claims have single dependencies in accordance with U.S. patent practice, each of the features in any of the dependent claims can be combined with each of the features of other dependent claims or the main claim.

The invention claimed is:

1. A system for providing healthcare asset intelligence, the system comprising:
   at least one processing device operable to format healthcare asset intelligence data accessed from a plurality of data sources at a data layer into a common format and provide the formatted healthcare asset intelligence data to at least one of a plurality of service components at a service component layer, wherein each of the plurality of data sources comprises one of a plurality of associated data formats, wherein the healthcare asset intelligence data is data related to management of healthcare assets, and wherein the system is configured according to a service-oriented architecture and uses service-oriented computing;
   the at least one processing device operable to perform intelligent analysis on the formatted healthcare asset intelligence data received at the at least one of the plurality of service components at the service component layer, wherein each of the plurality of service components is associated with a distinct task; and
   the at least one processing device operable to provide healthcare asset intelligence by at least one of creating a new service application and customizing an existing service application at a service application layer comprising a plurality of service applications, wherein one or more of the new service application is created and the existing service application is customized by selecting, based on a user input, at least one available service component from the plurality of service components at the service component layer, wherein each of the plurality of service components is operable to be reused when available by one or more of the plurality of service applications,
   wherein each of the data layer, the service component layer, and the service application layer function independently.

2. The system of claim 1, wherein the service component layer has serial access to the data layer.

3. The system of claim 1, wherein the service component layer is further adapted to manage the plurality of service components.

4. The system of claim 1, wherein the service component layer is further adapted to integrate at least two of the plurality of service components for use by the service application in providing the healthcare asset intelligence.

5. The system of claim 4, wherein the at least two of the plurality of service components are stored at locations that are remote from one another.

6. The system of claim 1, wherein the data layer is adapted to comprise a data warehouse, wherein the data warehouse is adapted to integrate a first set of data stored in a first data source and a second set of data stored in a second data source.

7. The system of claim 6, wherein the data warehouse is adapted to organize data from the first and second data sources according to a clustering factor.

8. The system of claim 7, wherein the first and second data sources are located remotely from one another.

9. The system of claim 1, wherein the at least one processing device is operable to at least one of encrypt, integrate and filter the healthcare asset intelligence data.

10. The system of claim 1, wherein the data layer, the service component layer, and the service application layer are stored at a centralized site.

11. The system of claim 1, wherein at least one of the plurality of service components is a rule processor unit adapted to generate an alarm based at least in part on an application of a rule to the healthcare asset intelligence data.

12. The system of claim 1, wherein at least one of the plurality of service components is adapted to process the healthcare asset intelligence data.

13. A method for providing healthcare asset intelligence, the method comprising:
   selecting, by at least one processing device based on a user input, at least one available service component from a plurality of service components to at least one of create a new service application and customize an existing service application, wherein each of the plurality of service components is operable to be reused when available by one or more of a plurality of service applications, wherein the selected at least one service component is adapted to acquire healthcare asset intelligence data from a data warehouse, the data warehouse including the healthcare asset intelligence data from a plurality of data sources located at a plurality of remote locations; and
   configuring, by the at least one processing device, the at least one of the created new service application and the customized existing service application based at least in part on the selected at least one service component using service-oriented computing, wherein the plurality of service components is in a service-oriented architecture, and wherein the selected service application is adapted to generate the healthcare asset intelligence using the selected at least one service component.

14. A method for providing healthcare asset intelligence, the method comprising:
   performing by at least one processing device, at least:
      creating a data warehouse by integrating a plurality of data sources located at a plurality of remote locations;
      selecting at least one available service component from a plurality of service components to at least one of create a new service application and customize an existing service application, wherein each of the plurality of service components is operable to be reused when available by one or more of a plurality of service applications;

acquiring healthcare asset intelligence data from the data warehouse using the selected at least one service component, wherein the selected at least one service component is associated with a service application selected from the plurality of service applications;

processing the acquired healthcare asset intelligence data using the selected at least one service component in a service-oriented architecture; and generating the healthcare asset intelligence based at least in part on the processing of the acquired healthcare asset intelligence data using service-oriented computing.

15. The method of claim 14, wherein the at least one service component is a plurality of service components, and wherein the plurality of service components serially access the healthcare asset intelligence data.

16. The method of claim 14, wherein the at least one service component and the data warehouse are stored at a centralized site.

17. The method of claim 14, wherein the healthcare asset intelligence is further based at least in part on an application of a rule to the acquired healthcare asset intelligence data.

18. The method of claim 14, further comprising:
organizing the acquired healthcare asset intelligence data according to a cluster factor.

19. The method of claim 14, further comprising:
preprocessing the acquired healthcare asset intelligence data.

20. The method of claim 14, further comprising:
displaying the healthcare asset intelligence on a user interface.

21. A non-transitory computer-readable medium including a set of instructions for execution on a computer, the set of instructions comprising:

a data warehouse creation routine configured to create a data warehouse by integrating a plurality of data sources located at a plurality of remote locations;

a service component selection routine configured to select at least one available service component from a plurality of service components to at least one of create a new service application and customize an existing service application, wherein each of the plurality of service components is operable to be reused when available by one or more of a plurality of service applications;

a data acquisition routine configured to acquire healthcare asset intelligence data from the data warehouse using the selected at least one service component, wherein the selected at least one service component is associated with a service application selected from the plurality of service applications;

a processing routine configured to process the acquired healthcare asset intelligence data based at least in part on the selected service application using a service-oriented architecture; and an intelligence generation routine configured to generate healthcare asset intelligence based at least in part on the processing routine using service-oriented computing and the service-oriented architecture.

* * * * *